United States Patent
Tiwari et al.

(10) Patent No.: US 10,662,475 B2
(45) Date of Patent: May 26, 2020

(54) COMPOSITIONS AND METHODS FOR THE TREATMENT AND PREVENTION OF ANTIPSYCHOTIC MEDICATION-INDUCED WEIGHT GAIN

(71) Applicant: Centre for Addiction and Mental Health, Toronto (CA)

(72) Inventors: Arun K. Tiwari, Toronto (CA); Eva J. Brandl, Toronto (CA); Nabilah I. Chowdhury, Toronto (CA); Vanessa F. Gonçalves, Toronto (CA); Jennie G. Pouget, Toronto (CA); James L. Kennedy, Toronto (CA); Daniel J. Mueller, Toronto (CA); Clement C. Zai, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 285 days.

(21) Appl. No.: 15/122,101

(22) PCT Filed: Feb. 27, 2015

(86) PCT No.: PCT/CA2015/050145
§ 371 (c)(1),
(2) Date: Aug. 26, 2016

(87) PCT Pub. No.: WO2015/127557
PCT Pub. Date: Sep. 3, 2015

(65) Prior Publication Data
US 2017/0073755 A1    Mar. 16, 2017

Related U.S. Application Data

(60) Provisional application No. 62/059,358, filed on Oct. 3, 2014, provisional application No. 62/056,250, filed on Sep. 26, 2014, provisional application No. 61/946,003, filed on Feb. 28, 2014.

(51) Int. Cl.
| | | |
|---|---|---|
| C12Q 1/68 | (2018.01) | |
| C12Q 1/6883 | (2018.01) | |
| G16B 20/00 | (2019.01) | |
| G01N 33/50 | (2006.01) | |

(52) U.S. Cl.
CPC ....... *C12Q 1/6883* (2013.01); *G01N 33/5091* (2013.01); *G16B 20/00* (2019.02); *C12Q 2600/106* (2013.01); *C12Q 2600/156* (2013.01)

(58) Field of Classification Search
None
See application file for complete search history.

(56) References Cited

U.S. PATENT DOCUMENTS

2003/0104453 A1    6/2003    Pickar et al.

FOREIGN PATENT DOCUMENTS

| WO | WO-2006/063332 A2 | 6/2006 |
| WO | WO-2006/063332 A3 | 6/2006 |

OTHER PUBLICATIONS

Cooper et al; Journal of Psychopharmacology, vol. 30, pp. 717-748; 2016.*
International search report issued in PCT/CA2015/050145 dated May 22, 2015.
Extended European Search Report dated Jul. 31,2017 for EP Application No. 15754639.1, filed Feb. 27, 2015, 8 pages.
Goncalves, V. et al. (2014). "A Hypothesis-Driven Association Study of 28 Nuclear-Encoded Mitochondrial Genes with Antipsychotic-Induced Weight Gain in Schizophrenia," *Neuropsychopharmacology* 39(6):1347-1354.
Lykkegaard, K. et al., (2008). "The once-daily human GLP-1 analog, liraglutide, reduces olanzapine-induced weight gain and glucose intolerance." *Schizophen. Res.* 103:94-103.
Yamanaka, A. et al., (2003). "Hypothalamic orexin neurons regulate arousal according to energy balance in mice." Neuron 38:701-713.
Gut, P. et al., (2013). "Whole-organism screening for gluconeogenesis identifies activators of fasting metabolism." *Nat. Chem. Bio.* 9(2):97-104.
Fang, F. et al., (2017). "Is there a 'weight neutral' second-generation antipsychotic for bipolar disorder?" *Exp. Rev. Neurothera.* 17:4, 407-418, DOI:10.1080/14737175.2016.1276284.
Bak, M. et al., (2014). "Almost all antipsychotics result in weight gain: A meta-analysis." *PLoS One* 9(4):e94112.doi:10.1371/journal. pone.0094112.
"Thermo-Scientific DyNAmo SYBR Green 2-Step qRT-PCR Kit Technical Manual." ThermoScientific, Jan. 1, 2011. (Jan. 1, 2011).

* cited by examiner

*Primary Examiner* — Jehanne S Sitton
(74) *Attorney, Agent, or Firm* — Muriel Liberto, Esq.; Mintz Levin Cohn Ferris Glovsky and Popeo, P.C.

(57) ABSTRACT

The invention provides methods and compositions for the treatment of a subject having a psychiatric disease or disorder based upon the subject's genotype and/or the number of risk alleles carried by the subject, which risk alleles have been found by the present inventors to predispose a subject to antipsychotic medication induced weight gain (AIWG). The methods of the invention also provide for different treatments, or different treatment regimens, for the subject depending on the subject's risk of AIWG. Related compositions, in the form of kits, systems, and computer-readable media are also provided.

10 Claims, 1 Drawing Sheet
Specification includes a Sequence Listing.

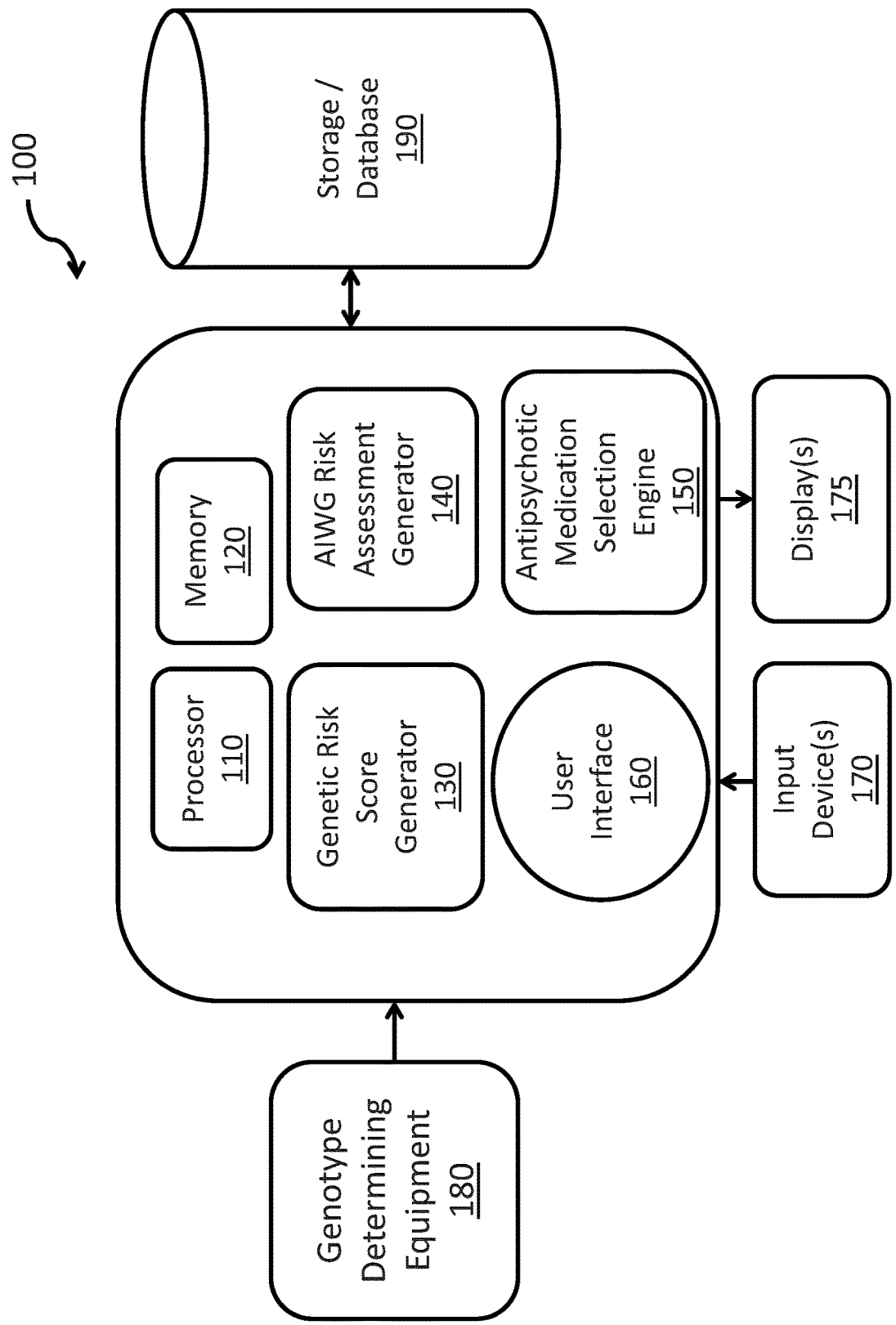

COMPOSITIONS AND METHODS FOR THE TREATMENT AND PREVENTION OF ANTIPSYCHOTIC MEDICATION-INDUCED WEIGHT GAIN

CROSS-REFERENCES TO RELATED APPLICATIONS

This application is a national stage entry, filed under 35 U.S.C. § 371, of International Application No. PCT/US2015/050145, filed on Feb. 27, 2015, and claims the benefit of and priority to U.S. Provisional Patent Application No. 61/946,003, filed Feb. 28, 2014, U.S. Provisional Patent Application No. 62/056,250, filed Sep. 26, 2014 and U.S. Provisional Application No. 62/059,358, filed Oct. 3, 2014, the entire contents of each are hereby incorporated herein by reference in their entireties and for all purposes.

SEQUENCE LISTING

The instant application contains a Sequence Listing which has been submitted electronically in ASCII format and is hereby incorporated by reference in its entirety. Said ASCII copy, created on Mar. 14, 2020, is named 52237-501N01US_Sequence_Listing_ST25.txt and is 4,453 bytes in size.

FIELD OF INVENTION

The present invention relates to the field of psychiatry. In particular, the invention relates to methods and compositions for the treatment and prevention of antipsychotic medication-induced weight gain based upon one or more genetic polymorphisms associated with such weight gain in human subjects.

BACKGROUND OF THE INVENTION

Antipsychotics are widely used for treating psychiatric disorders including schizophrenia, mood, bipolar disorders and autism. Most second generation antipsychotic medications have been associated with substantial weight gain and metabolic disturbances, increasing the risk for premature death (Lencz and Malhotra, 2009; Muller and Kennedy, 2006). The high prevalence of over 30% of treated individuals experiencing significant weight gain makes these side effects one of the leading causes of patient non-compliance leading to increased treatment costs. There are currently no biomarkers available for antipsychotic-induced weight gain (AIWG) and the strongest predictor remains a positive family history of AIWG in first-degree relatives. Twin and family studies have consistently pointed to high heritability suggesting a possible role of genetic factors in AIWG (Gebhardt et al., 2010).

GLP-1

Glucagon-like peptide 1 (GLP-1) is an important peptide involved in central regulation of food intake as well as in peripheral glucose regulation. GLP-1 is an incretin hormone which is released from small intestinal L-cells together with glucose-dependent insulinotropic polypeptide (GIP) following food intake. It acts on G-protein coupled GLP-1 receptors (GLP-1R), which are widely expressed in the central nervous system (CNS), pancreas, heart, gastrointestinal tract, kidneys and other tissues (Phillips and Prins 2011). GLP-1 reduces food intake, likely mediated through inhibition of central AMP-activated kinase following activation of GLP-1R in the hindbrain (Burmeister et al., 2013).

Besides augmenting insulin secretion, GLP-1 inhibits glucagon secretion and delays gastric emptying (Phillips and Prins 2011). The insulinotropic effect depends on blood glucose levels (Fu et al. 2013), and impaired GLP-1 induced insulin secretion has been found in type 2 diabetes patients (Herzberg-Schafer et al. 2012). Interestingly, an antipsychotic-like effect of a GLP-1 receptor agonist has recently been described in a mouse model (Dixit et al. 2013).

Several previous studies have investigated effects of antipsychotics on GLP-1. Antipsychotics with high or medium-high risk for antipsychotic-induced weight gain (AIWG) such as olanzapine (Smith et al. 2011), clozapine or quetiapine (Smith et al. 2009) have been shown to decrease GLP-1 levels in rat models. These effects seem to occur after a longer treatment period, since studies with short-term treatment did not show an impact of olanzapine on GLP-1 levels (Vidarsdottir et al. 2010; van der Zwaal et al. 2012). Recent research has indicated a beneficial effect of GLP-1 analogs for treatment of AIWG in animal models (Lykkegaard et al. 2008). Clinical studies showed that GLP-1 analogs were effective to induce weight loss not only in subjects with type 2 diabetes (Flint et al. 2013), but also in non-diabetic patients (Astrup et al. 2012; Vilsboll et al. 2012). The gene encoding GLP-1, GCG, is located on chromosome 2q36-37. GCG encodes a preproprotein which is cleaved into four different proteins involved in glucose homeostasis (glucagon, GLP-1, GLP-2, oxyntomodulin). Genetic variation in GCG has previously been associated with weight, insulin, GLP-1 and glucagon levels (Torekov et al. 2011). The human GLP-1 receptor gene GLP1R is located on chromosome 6p21. Variation in this gene has been associated with morning cortisol levels (Sheikh et al. 2010) and altered insulin secretion following GLP-1 infusion (Sathananthan et al. 2010). In animal models, genetic variation in GLP1R influenced food intake (Kumar et al. 2007) and gastric emptying (Kumar et al. 2008). On the other hand, glp1r-deficient mice showed normal feeding behavior in an earlier study (Scrocchi et al. 1996). Despite these preliminary findings, GCG and GLP1R are interesting candidate genes for AIWG due to their implication in food intake and glucose metabolism.

Orexin/Hypocretin

The orexin system includes the orexin gene coding for pre-pro-orexin which is cleaved into two polypeptides, Orexin A (OXA, hypocretin 1, 33 amino acids) and Orexin B (OXB, hypocretin 2, 28 amino acids). The biological action of the orexin peptides is mediated through two G-protein coupled receptors orexin receptor 1 (OX1R or HCRTR1) and orexin receptor 2 (OX2R or HCRTR2; (Sakurai and Mieda 2011; Kukkonen 2013; Perez-Leighton et al. 2013)). OXA has higher affinity for OX1R whereas OXA and OXB have equal affinity for OX2R. Orexins are primarily expressed in the lateral hypothalamic area, a region associated with feeding behavior and arousal. Decreased extracellular glucose levels activate orexin neurons whereas increased glucose concentrations have the opposite effect (Yamanaka et al. 2003; Burdakov et al. 2005). Similarly, the orexigenic peptide ghrelin activates 60% of orexin neurons, whereas the anorexigenic peptide leptin inhibits most orexin neurons (Yamanaka et al. 2003). Increased level of orexin mRNA is observed in fasting conditions and intracerebrovascular (ICV) injection of orexin during light period induces feeding behavior in rats and mice. Furthermore, ICV injection of anti-orexin antibody reduces food intake (Yamada et al. 2000). In accordance with this observation, mice lacking orexin neurons exhibit hypophagia, lower levels of spontaneous physical activity (SPA) and develop late-onset obesity on a regular diet (Hara et al. 2001; Akiyama et al. 2004). Furthermore, overexpression of the pre-pro orexin gene leads to resistance to obesity induced by consumption of high fat diet. This protective effect has been primarily attributed to increased energy expenditure (Funato et al. 2009; Perez-Leighton et al. 2013).

Orexin receptors are expressed in several regions in the brain. OX1R, compared to OX2R, are predominant in the locus coeruleous, paraventricular thalamic nucleus and bed nucleus of the stria terminalis. OX2R are mainly expressed in the arcuate nucleus (ARC), paraventricular nucleus and lateral hypothalamic area (Marcus et al. 2001; Funato et al. 2009). The OX2R has been shown to play a major role in preventing high fat diet induced obesity and insulin insensitivity in mice (Funato et al. 2009). Similarly, OX2R agonist administration to wildtype-mice on a high fat diet suppressed food intake and led to significantly less fat mass. In the same study mice with OX1R deletion showed improved glucose tolerance and insulin sensitivity on a high fat diet suggesting that OX1R may also have a role in mediating the effect of high fat diet on glucose metabolism (Funato et al. 2009). Overall OX2R appears to have a major role in adverse dietary conditions with OX1R making minor contribution. The orexin gene and its receptors have also been associated to narcolepsy in mice, dogs and humans (Kukkonen 2013). Interestingly, individuals with narcolepsy have decreased caloric intake but have a higher body mass index and increased incidence of metabolic syndrome (Schuld et al. 2000; Nishino 2007).

The orexin system is modulated by leptin via its receptors, especially OX2R (Funato et al. 2009), and sends excitatory signals to neuropeptide Y (NPY) expressing neurons in the ARC (Muroya et al. 2004). In addition, it has been shown that the orexin system also interacts with endocannabinoids as injection of the cannabinoid receptor type 1 (CB1) antagonist, rimonabant, abolishes feeding induced by intracerebroventricular orexin-A injection (Crespo et al. 2008). Recently Cristino et al., (2013), reported that in murine models of obesity (leptin deficient), increased endocannabinoid synthesis causes activation of CB1 receptors (Cristino et al. 2013). This reduces inhibition of orexinergic neurons and enhances orexin-A release leading to hyperphagia and increased body weight gain. Thus, the orexin system interacts with both NPY and the CB1 expressing neurons.

Antipsychotics associated with weight gain increase activity in orexin neurons compared to antipsychotics with no weight gain liability (Fadel et al. 2002). In addition, antipsychotics associated with higher risk of weight gain (e.g. clozapine and olanzapine) activated orexin neurons significantly more than antipsychotics with relatively less AIWG risk (e.g. risperidone). Similarly, in female Sprague Dawley rats injected with olanzapine 50% of the neurons activated in the perifornical region of lateral hypothalamus are orexin A positive (Stefanidis et al. 2009). This suggests that antipsychotics with weight gain liability modulate orexin neurons. However, the impact of genetic variation in the orexin system on AIWG has not been investigated to date.

NDUF S1

The NDUFS1 gene (NADH dehydrogenase (ubiquinone) Fe—S protein 1, 75 KDa) is part of the complex I of OXPHOS. This gene encodes the largest and one of the "core subunits" of this complex and the protein is located in the iron-sulfur fragment of the enzyme complex (Smeitink et al., 1998). NDUFS1 is part of the hydrophilic arm of the complex which is responsible for the transfer of electrons (Finel, 1998, Scola et al., 2013). Reduced levels of NDUFS1 mRNA and down-regulation of the protein in postmortem brain from schizophrenia patients have been reported (Maurer et al., 2001; Prabakaran et al., 2004).

Mutations in NDUFS1 have been associated with isolated complex I deficiency (Hoefs et al., 2010), and dysfunction in the cellular oxidative metabolism with increased mitochondrial Reactive Oxygen Species (mROS) production (Iuso et al., 2006). The effect of variants on mROS production may be of special importance since it may influence the energy homeostasis in the hypothalamus. For example, mROS are involved in the regulation of the ATP-dependent potassium channel in POMC neurons, an important step to neuronal depolarization and downstream events that will lead to decreased food intake. Besides that, in NPY neurons, the buffering of mROS appears to be crucial to keep active the ghrelin-dependent gene expression and downstream events to stimulate food intake.

TSPO

The translocator protein-18 kDa (TSPO, chr22: 43547520-43559248 Genome Reference Consortium Build 37) is a housekeeping gene. While the precise functions of TSPO are an active area of research, it is known to play a key role in steroid biosynthesis. TSPO is expressed by many tissues throughout the body, and at particularly high levels in steroidogenic tissues such as the adrenal glands and gonads. In the brain, TSPO is expressed selectively by activated microglia and reactive astrocytes, mediators of the brain's inflammatory response, which has led to the use of TSPO as an in vivo marker of neuroinflammation in PET imaging studies (reviewed by Venneti et al., 2013). At the subcellular level TSPO is localized primarily to the outer mitochondrial membrane, where it forms a multimeric complex with voltage-dependent anion channel (VDAC) and adenine nucleotide transporter (ANT) (McEnery et al., 1992).

There is evidence that TSPO plays a role in weight regulation, possibly through its effect on mitochondrial metabolism. In the leptin-deficient ob/ob mouse, an established animal model of obesity, increased TSPO binding capacity was observed in the hippocampus and hypothalamus (Giannaccini et al., 2011). Furthermore, TSPO ligands PK1195 and Ro5-4864 were recently identified as key regulators of whole-body energy control in zebra fish and mice (Gut et al., 2013). In high-fat diet induced obese mice, PK1195 treatment significantly lowered lipid accumulation in the liver, free and LDL cholesterol, and blood glucose levels (Gut et al., 2013). Taken together, these data suggest that TSPO may be a key factor in regulating energy homeostasis and body weight.

The atypical antipsychotic clozapine has been shown to increase TSPO binding capacity in the hippocampus and hypothalamus as well as in steroidogenic tissues in rats, and this increased binding capacity corresponded with increased steroid synthesis in vitro (Danovich et al., 2008). Interestingly, neurosteroids mediate response to clozapine and olanzapine in animal studies (Marx et al., 2000, Ugale et al., 2004, Marx et al., 2003, Marx et al., 2006), and human studies suggest that adjunct treatment with the neurosteroid pregnenolone improves symptoms of schizophrenia (Marx et al., 2009, Marx et al., 2011).

There is a need in the art to identify genetic markers associated with weight gain. Further, there is a need in the art for genetic markers associated with antipsychotic-induced weight gain. Further, there is a need in the art for genetic diagnostic markers for antipsychotic-induced weight gain that provide physicians and other health care professionals with the opportunity to provide educated decisions for prescribing medications in treatment regimens. Moreover, there is a need in the art for personalized medicine approaches that lower the risk of developing antipsychotic induced weight gain and related ailments such as diabetes and cardiovascular disease.

SUMMARY OF THE INVENTION

The present invention provides methods, including computer implemented methods, and compositions, including computer program products and computer systems, for improving therapeutic outcomes for patients being treated or in need of treatment with one or more medications to alleviate one or more symptoms of a psychiatric disease or disorder, also referred to herein as "psychiatric patients". In one embodiment, the invention provides improvements in therapeutic outcomes by preventing or reducing weight gain in a psychiatric patient being treated with one or more antipsychotic medications. In one embodiment, the invention provides methods for selecting an antipsychotic medication for a psychiatric patient that minimizes the psychiatric patient's risk of clinically significant weight gain induced by the medication. In this context, a patient is at high risk of clinically significant weight gain if they are likely to experience a weight gain of 7% or greater from their baseline weight (before taking the medication). A patient is at intermediate risk if they are likely to experience a weight gain of between 2% and 7%, and a patient is at low risk if they are likely to experience a weight gain of less than 2%, or even lose weight. Patients characterized as being in the high risk group according to the methods described herein should use medications such as olanzapine and clozapine very cautiously, or avoid their use in favor of, for example, other medications that are not associated with weigh gain. In this context, use very cautiously means that the medication should be given initially at a dose lower than recommended, if it is used at all, and the patients should be closely monitored for weight gain. Ideally, medications such as olanzapine and clozapine should be avoided in patients characterized as at high risk of weight gain. Such patients should also use medications such as quetiapine, risperidone, and paliperidone with caution. In this context, use with caution means that medication can initially be given at the recommended dose and the patient should be monitored for weight gain. In accordance with these methods, the patient is first categorized as being at risk or not at risk for weigh gain using an algorithm that incorporates data attributes characterizing the patient's genotype at a set of SNPs as described herein. Thus, the invention also provides methods of reducing a psychiatric patient's risk of clinically significant weight gain induced by an antipsychotic medication as well as methods for determining a psychiatric patient's susceptibility to such weight gain by identifying at-risk patients and providing an assessment of that risk, as described herein. Also provided are methods for designing a therapeutic regimen for a patient that minimizes the risk of weight gain by identifying at-risk patients, providing an assessment of that risk, and further categorizing a set of medications according to the relative risk of weight gain presented by each for that patient. The methods may also include generating and outputting a report identifying a patient according to risk of clinically significant weight gain induced by an antipsychotic medication, assessment of that risk, and medications categorized according to the relative risk of weight gain presented by each for the patient.

In one embodiment, the invention provides a method of selecting an antipsychotic medication or administering an antipyschotic medication to a subject in need thereof comprising: (1) determining or receiving the subject's genotype for at least one SNP selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2); (2) assigning an AIWG risk assessment to the subject, and (3) selecting or administering an antipsychotic medication to the subject based on the subject's AIWG risk assessment such that antipsychotic medications having a tendency to induce weight gain are avoided in favor of those having little tendency to induce weight gain where the AIWG risk assessment indicates the subject is at risk for AIWG.

In one embodiment, in step (2), the subject is assigned an AIWG risk assessment of "high", "intermediate", or "low" based on the subject's total genetic risk score, defined as the sum of the individual risk scores of each genotype determined or received in step (1).

In one embodiment, in step (3), the antipsychotic medication is administered to the subject based on the subject's AIWG risk assessment as follows: (i) if the risk assessment is high, administer one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or administer risperidone, paliperidone, or quetiapine in combination with weight monitoring, and avoid administering clozapine and olanzapine; (ii) if the risk assessment is intermediate, administer one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or administer clozapine or olanzapine in combination with weight monitoring; and (iii) if the risk assessment is low, administer one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic.

In one embodiment, step (1) comprises determining or receiving the subject's genotype for rs3134701 (SEQ ID NO: 2) (HCRTR2), rs4142972 (SEQ ID NO: 3) (HCRTR2^2), or both. In one embodiment, step (1) comprises or consists of determining or receiving the subject's genotype for at least two SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2). In one embodiment, step (1) comprises or consists of determining or receiving the subject's genotype for at least two SNPs, one or both of which is selected from rs3134701 (SEQ ID NO: 2) (HCRTR2) and rs4142972 (SEQ ID NO: 3) (HCRTR2^2), and the remaining SNP is selected from the group consisting of rs13429709 (SEQ ID NO: 1) (GCG), rs6435326 (SEQ ID NO: 6) (NDUFS1), rs6971 (SEQ ID NO: 9) (TSPO), and rs279858 (SEQ ID NO: 14) (GABRA2).

In one embodiment, step (1) comprises or consists of determining or receiving the subject's genotype for a set of two SNPs, one or both of which is selected from rs3134701

(SEQ ID NO: 2) (HCRTR2) and rs4142972 (SEQ ID NO: 3) (HCRTR2^2), and the remaining SNP is selected from the group consisting of rs13429709 (SEQ ID NO: 1) (GCG), rs6435326 (SEQ ID NO: 6) (NDUFS1), rs6971 (SEQ ID NO: 9) (TSPO), and rs279858 (SEQ ID NO: 14) (GABRA2). In one embodiment, the set of two SNPs is selected from among the following:

rs3134701 (SEQ ID NO: 2) (HCRTR2) and rs4142972 (SEQ ID NO: 3) (HCRTR2^2);

rs3134701 (SEQ ID NO: 2) (HCRTR2) and rs6435326 (SEQ ID NO: 6) (NDUFS1);

rs4142972 (SEQ ID NO: 3) (HCRTR2^2) and rs6435326 (SEQ ID NO: 6) (NDUFS1);

rs3134701 (SEQ ID NO: 2) (HCRTR2) and rs13429709 (SEQ ID NO: 1) (GCG); and rs4142972 (SEQ ID NO: 3) (HCRTR2^2) and rs13429709 (SEQ ID NO: 1) (GCG).

In accordance with the embodiments where step (1) comprises or consists of determining or receiving the subject's genotype for a set of two SNPs, the subject is assigned an AIWG risk assessment of "high" if the subject has a total genetic risk score of at least 2, the subject is assigned an AIWG risk assessment of "intermediate" if the subject has a total genetic risk score of 1, and the subject is assigned an AIWG risk assessment of "low" if the subject has a total genetic risk score of 0.

In one embodiment, step (1) comprises or consists of determining or receiving the subject's genotype for at least three SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO). In one embodiment, step (1) comprises or consists of determining or receiving the subject's genotype for at least three SNPs, one or two of which is selected from rs3134701 (SEQ ID NO: 2) (HCRTR2) and rs4142972 (SEQ ID NO: 3) (HCRTR2^2), and the remaining SNP is selected from the group consisting of rs13429709 (SEQ ID NO: 1) (GCG), rs6435326 (SEQ ID NO: 6) (NDUFS1), and rs6971 (SEQ ID NO: 9) (TSPO).

In one embodiment, step (1) comprises or consists of determining or receiving the subject's genotype for a set of three SNPs, one or two of which is selected from rs3134701 (SEQ ID NO: 2) (HCRTR2) and rs4142972 (SEQ ID NO: 3) (HCRTR2^2), and the remaining selected from the group consisting of rs13429709 (SEQ ID NO: 1) (GCG), rs6435326 (SEQ ID NO: 6) (NDUFS1), and rs6971 (SEQ ID NO: 9) (TSPO). In one embodiment, the set of three SNPs is selected from the following:

rs3134701 (SEQ ID NO: 2) (HCRTR2), rs13429709 (SEQ ID NO: 1) (GCG), and rs6435326 (SEQ ID NO: 6) (NDUFS1);

rs4142972 (SEQ ID NO: 3) (HCRTR2^2), rs13429709 (SEQ ID NO: 1) (GCG), and rs6435326 (SEQ ID NO: 6) (NDUFS1);

rs3134701 (SEQ ID NO: 2) (HCRTR2), rs4142972 (SEQ ID NO: 3) (HCRTR2^2), and rs6435326 (SEQ ID NO: 6) (NDUFS1); and rs4142972 (SEQ ID NO: 3) (HCRTR2^2), rs6435326 (SEQ ID NO: 6) (NDUFS1), and rs6971 (SEQ ID NO: 9) (TSPO).

In accordance with the embodiments where step (1) comprises or consists of determining or receiving the subject's genotype for a set of three SNPs, the subject is assigned an AIWG risk assessment of "high" if the subject has a total genetic risk score of at least 3, an AIWG risk assessment of "intermediate" if the subject has a total genetic risk score of at least 2 but less than 3, and an AIWG risk assessment of "low" if the subject has a total genetic risk score of less than 2.

In one embodiment, step (1) comprises or consists of determining or receiving the subject's genotype for at least four SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO). In one embodiment, step (1) comprises or consists of determining or receiving the subject's genotype for at least four SNPs, one or two of which is selected from rs3134701 (SEQ ID NO: 2) (HCRTR2) and rs4142972 (SEQ ID NO: 3) (HCRTR2^2), and the remaining SNP is selected from the group consisting of rs13429709 (SEQ ID NO: 1) (GCG), rs6435326 (SEQ ID NO: 6) (NDUFS1), and rs6971 (SEQ ID NO: 9) (TSPO).

In one embodiment, step (1) comprises or consists of determining or receiving the subject's genotype for a set of four or five SNPs, one or two of which is selected from rs3134701 (SEQ ID NO: 2) (HCRTR2) and rs4142972 (SEQ ID NO: 3) (HCRTR2^2), and the remaining SNP is selected from the group consisting of rs13429709 (SEQ ID NO: 1) (GCG), rs6435326 (SEQ ID NO: 6) (NDUFS1), and rs6971 (SEQ ID NO: 9) (TSPO). In one embodiment, the set of SNPs is selected from one of the following:

rs3134701 (SEQ ID NO: 2) (HCRTR2), rs4142972 (SEQ ID NO: 3) (HCRTR2^2), rs13429709 (SEQ ID NO: 1) (GCG), and rs6971 (SEQ ID NO: 9) (TSPO);

rs3134701 (SEQ ID NO: 2) (HCRTR2), rs4142972 (SEQ ID NO: 3) (HCRTR2^2), rs13429709 (SEQ ID NO: 1) (GCG), and rs6435326 (SEQ ID NO: 6) (NDUFS1);

rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO);

rs3134701 (SEQ ID NO: 2) (HCRTR2), rs4142972 (SEQ ID NO: 3) (HCRTR2^2), rs13429709 (SEQ ID NO: 1) (GCG), rs6435326 (SEQ ID NO: 6) (NDUFS1), and rs6971 (SEQ ID NO: 9) (TSPO);

rs3134701 (SEQ ID NO: 2) (HCRTR2), rs13429709 (SEQ ID NO: 1) (GCG), rs6435326 (SEQ ID NO: 6) (NDUFS1), and rs6971 (SEQ ID NO: 9) (TSPO); and rs4142972 (SEQ ID NO: 3) (HCRTR2^2), rs13429709 (SEQ ID NO: 1) (GCG), rs6435326 (SEQ ID NO: 6) (NDUFS1), and rs6971 (SEQ ID NO: 9) (TSPO).

In accordance with the embodiments where step (1) comprises or consists of determining or receiving the subject's genotype for a set of four or five SNPs, the subject is assigned an AIWG risk assessment of "high" if the subject has a total genetic risk score of at least 4, an AIWG risk assessment of "intermediate" if the subject has a total genetic risk score of at least 2 but less than 4, and an AIWG risk assessment of "low" if the subject has a total genetic risk score of less than 2. In one embodiment, step (1) comprises or consists of determining or receiving the subject's genotype for at least five SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO).

In one embodiment, step (1) comprises or consists of determining or receiving the subject's genotype for at least six SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GA- BRA2). In one embodiment, step (1) further comprises or consists of determining or receiving the subject's genotype for one or more additional SNP's selected from rs489693 (SEQ ID NO: 11) (MC4R), rs806378 (SEQ ID NO: 12) (CNR1), and rs16147 (SEQ ID NO: 13) (NPY). In accordance with these embodiments, the subject is assigned an AIWG risk assessment of "high" if the subject has a total genetic risk score of at least 6, an AIWG risk assessment of "intermediate" if the subject has a total genetic risk score less than 6 but greater than 3, and an AIWG risk assessment of "low" if the subject has a total genetic risk score of 3 or less.

In one embodiment, step (1) comprises or consists of determining or receiving the subject's genotype for at least seven SNPs, the at least seven SNPs comprising at least four SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2) and three SNPs selected from rs489693 (SEQ ID NO: 11) (MC4R), rs806378 (SEQ ID NO: 12) (CNR1), and rs16147 (SEQ ID NO: 13) (NPY). In one embodiment, the seven SNPs are selected from rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs489693 (SEQ ID NO: 11) (MC4R), rs806378 (SEQ ID NO: 12) (CNR1), and rs16147 (SEQ ID NO: 13) (NPY). In accordance with these embodiments, the subject is assigned an AIWG risk assessment of "high" if the subject has a total genetic risk score of at least 5, an AIWG risk assessment of "intermediate" if the subject has a total genetic risk score less than 5 but at least 2, and an AIWG risk assessment of "low" if the subject has a total genetic risk score of less than 2.

In accordance with any of the embodiments comprising an AIWG risk assessment of "intermediate", the method may further comprise weight monitoring in combination with one or more of (i) the administration of an appetite suppressant or hypoglycemic medication selected from the group consisting of a sulfonylurea, thiazolidinedione, alpha glucosidase inhibitor, and metformin; (ii) a diet plan; and (iii) an exercise regimen.

In an embodiment of any of the foregoing methods, the step of determining the subject's genotype for at least one SNP comprises a step of contacting a set of SNP-specific primers with DNA extracted from a sample from the subject, allowing the primers to bind to the DNA, and amplifying the SNP containing regions of the DNA using a polymerase chain reaction. In one embodiment, the set of SNP-specific primers comprises primers for amplifying two or more SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2). In one embodiment, at least one of the set of SNP-specific primers comprises primers for amplifying rs3134701 (SEQ ID NO: 2) (HCRTR2) or rs4142972 (SEQ ID NO: 3) (HCRTR2^2). In one embodiment, the set of SNP-specific primers comprises primers for amplifying at least the SNPs defined by rs13429709 (SEQ ID NO: 1) (GCG), rs3134701 (SEQ ID NO: 2) (HCRTR2), rs4142972 (SEQ ID NO: 3) (HCRTR2^2), and rs6435326 (SEQ ID NO: 6) (NDUFS1). In a further embodiment, the set of SNP-specific primers comprises primers for amplifying the set of SNPs defined by rs13429709 (SEQ ID NO: 1) (GCG), rs3134701 (SEQ ID NO: 2) (HCRTR2), rs4142972 (SEQ ID NO: 3) (HCRTR2^2), and rs6435326 (SEQ ID NO: 6) (NDUFS1) and one or more additional SNPs defined by rs489693 (SEQ ID NO: 11) (MC4R), rs806378 (SEQ ID NO: 12) (CNR1), and rs16147 (SEQ ID NO: 13) (NPY).

In an embodiment of any of the foregoing methods, the step of receiving the subject's genotype for at least one SNP comprises receiving, in a computer system, the patient's genotype for the at least one SNP, the computer system comprising a database which comprises a plurality of antipsychotic medication profiles, each medication profile comprising information about the medication's side effects, including its tendency to induce weight gain, and optionally including additional information about the medication such as interactions and adverse events. In one embodiment, step 2 is also performed using said computer system and the method further comprises the step of outputting the identity of an antipsychotic medication for administering to the patient. In one embodiment, a user enters the patient's genotype in the computer system. In one embodiment, the patient's genotype is received directly from equipment used in determining the patient's genotype.

The invention also provides a non-transitory computer readable medium containing executable instructions that when executed cause a processor to perform operations comprising assigning an AIWG risk assessment to a subject based on a subject's genotype at one or more SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2). In one embodiment, the one or more SNPs comprises rs3134701 (SEQ ID NO: 2) (HCRTR2) and/or rs4142972 (SEQ ID NO: 3) (HCRTR2^2). In one embodiment, the one or more SNPs is at least seven SNPs, the at least seven SNPs comprising at least four SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2) and three SNPs defined by rs489693 (SEQ ID NO: 11) (MC4R), rs806378 (SEQ ID NO: 12) (CNR1), and rs16147 (SEQ ID NO: 13) (NPY). In one embodiment, the seven SNPs are defined by rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs489693 (SEQ ID NO: 11) (MC4R), rs806378 (SEQ ID NO: 12) (CNR1), and rs16147 (SEQ ID NO: 13) (NPY).

The invention also provides a kit of parts comprising a set of nucleotides suitable for amplifying at least two SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2). In one embodiment, the set of nucleotides includes nucleotides suitable for amplifying at least one of rs3134701 (SEQ ID NO: 2) (HCRTR2) and rs4142972 (SEQ ID NO: 3) (HCRTR2^2). In one embodiment, the set of nucleotides includes nucleotides suitable for amplifying at least seven SNPs, the at least seven SNPs comprising at least four SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2) and three SNPs defined by rs489693 (SEQ ID NO: 11) (MC4R), rs806378 (SEQ ID NO: 12) (CNR1), and rs16147 (SEQ ID NO: 13) (NPY). In one embodiment, the seven SNPs are defined by rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs489693 (SEQ ID NO: 11) (MC4R), rs806378 (SEQ ID NO: 12) (CNR1), and rs16147 (SEQ ID NO: 13) (NPY).

In one embodiment, the invention provides a method for selecting an antipsychotic medication for a subject in need of treatment for a psychiatric disease or disorder, the methods comprising selecting an antipsychotic medication based on the subject's AIWG risk assessment such that antipsychotic medications having a high tendency to induce weight gain are avoided in favor of those having a low or intermediate tendency to induce weight gain. In one embodiment, where the subject has a high AIWG risk assessment, the method comprises selecting one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or selecting risperidone, paliperidone, or quetiapine in combination with weight monitoring, and avoiding clozapine and olanzapine. In one embodiment, where the AIWG risk assessment is intermediate, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or selecting clozapine or olanzapine in combination with weight monitoring. In one embodiment, where the AIWG risk assessment is low, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic.

In one embodiment, the invention provides a method for determining a subject's susceptibility to antipsychotic medication induced weight gain based on the subject's AIWG risk assessment. In one embodiment, where the subject has a high AIWG risk assessment, the subject's susceptibility is determined to be high and the method comprises recommending for the subject one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or recommending risperidone, paliperidone, or quetiapine in combination with weight monitoring, and recommending that the subject avoid clozapine and olanzapine. In one embodiment, where the AIWG risk assessment is intermediate, the subject's susceptibility is determined to be intermediate and the methods comprise recommending for the subject one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or recommending clozapine or olanzapine in combination with weight monitoring. In one embodiment, where the AIWG risk assessment is low, the subject's susceptibility is determined to be low and the methods comprise recommending for the subject one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic.

In one embodiment, the invention provides a method for designing a therapeutic regimen for a subject in need of treatment with an antipsychotic medication, the methods comprising selecting an antipsychotic medication based on the subject's AIWG risk assessment such that antipsychotic medications having a high tendency to induce weight gain are avoided in favor of those having a low or intermediate tendency to induce weight gain. In one embodiment, where the subject has a high AIWG risk assessment, the method comprises selecting one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or selecting risperidone, paliperidone, or quetiapine in combination with weight monitoring, and avoiding clozapine and olanzapine. In one embodiment, where the AIWG risk assessment is intermediate, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or selecting clozapine or olanzapine in combination with weight monitoring. In one embodiment, where the AIWG risk assessment is low, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic. In embodiments where weight monitoring forms part of the therapeutic regimen, additional elements such as diet and exercise may be added to the regimen to mitigate weight gain.

BRIEF DESCRIPTION OF THE FIGURE

FIG. 1 is a block diagram of a system in accordance with some embodiments of the present subject matter.

DETAILED DESCRIPTION

The present subject matter relates in part to the discovery of certain genetic markers that are informative regarding a subject's risk of experiencing a clinically significant weight gain during treatment with an antipsychotic medication. The genetic markers are in the form of single nucleotide polymorphisms (SNPs) determined by the inventors to be associated with clinically significant weight gain in human subjects treated with antipsychotic medications, also referred to herein as "psychiatric patients". Clinically significant weight gain associated with antipsychotic medication treatment is referred to herein as "anti-psychotic-induced weight gain" or "AIWG".

The methods of the invention provide an output indicating a subject's risk of AIWG based upon the subject's genotype at one or more SNPs, as described herein, and optionally one or more additional subject specific factors as described below. In one embodiment, the subject is a psychiatric patient. As used herein, the term "psychiatric patient" refers to a human subject having a diagnosis indicating that the subject is in need of treatment with one or more medications to alleviate one or more symptoms of a psychiatric disease or disorder. In one embodiment, the one or more medications is an antipsychotic medication. The output of risk provided by the methods of the invention is referred to herein as the "AIWG risk assessment". Thus, the AIWG risk assessment incorporates information about the subject's genotype at one or more SNPs. The AIWG risk assessment may also incorporate other information about the subject, as discussed below.

In one embodiment, the methods of the invention provide a model which incorporates information about the subject's genotype for at least 1, at least 2, at least 3, at least 4, at least 5, at least 6, or at least 7 SNPs as described herein. In one embodiment, the model incorporates information about 1, 2, 3, 4, 5, 6, 7 or 8 SNPs. In one embodiment, the model incorporates information about 4 or 5 SNPs or information about 6, 7, or 8 SNPs. In one embodiment, the model incorporates information about at least 6 or at least 7 SNPs.

In one embodiment, the methods of the invention further comprise an output indicating the set of antipsychotic medications that is administered or should be administered to the subject and the set of antipsychotic medications that should be avoided based upon the subject's AIWG risk assessment as determined by the methods of the present invention.

In one embodiment, the invention provides methods that comprise administering or selecting one or more antipsychotic medications based upon a subject's AIWG risk assessment. In one embodiment, where the subject's AIWG risk assessment is "high" the methods comprise administering or selecting a medication having a low risk of inducing weight gain, or administering or selecting a medication having an intermediate risk of inducing weight gain in combination with weight monitoring. In another embodiment, where the subject's AIWG risk assessment is "intermediate" the methods comprise administering or selecting a medication having a low or intermediate risk of inducing weight gain.

A subject's weight gain is considered to be clinically significant if it increases by 7% or more after the subject has been treated with one or more antipsychotic medications for a period of time, compared to the subject's baseline weight. The subject's baseline weight is the subject's weight before treatment with the one or more antipsychotic medications. In one embodiment, the clinically significant weight gain is between 7 and 10% of the subject's baseline weight. In one embodiment, the clinically significant weight gain is between 10 and 15% of the subject's baseline weight. In one embodiment, the clinically significant weight gain is greater than 15% of the subject's baseline weight. Generally, the period of antipsychotic medication treatment comprises a period of months, for example, 2, 3, 4, 5, or 6 months, or more, for example 12 or 24 months.

In the context of the present invention, the subject is a human subject, and more specifically an adult subject, a pediatric subject, or an elderly subject, as those terms are understood in the medical arts. In certain embodiments, the subject is further defined according to the subject's ethnicity. For example, in one embodiment the subject self-identifies or is genetically determined to be a member of an ethnic group selected from African, North African, Southern African, European, Western European, Northern European, Asian, Japanese, Han Chinese, and Korean. Preferably, the subject's ethnicity is determined by genetic analysis according to routine methods. In one embodiment, the subject is of European ethnicity. In one embodiment, the subject is of African ethnicity. In one embodiment, the subject is of Asian ethnicity. In another embodiment, the subject is of non-European ethnicity. In this context, the terms ethnicity and ancestry are used interchangeably.

Preferably, the methods of the invention are directed to subjects in need of treatment with one or more antipsychotic medications. In one embodiment, the subject in need of treatment is one who does not present with any symptoms, or does not present with sufficient symptoms of a psychiatric disease or disorder to have a diagnosis but is at increased risk of developing a psychiatric disease or disorder because of a family history of such disease or disorder. In one embodiment, the subject in need of treatment is one who presents with sufficient symptoms of a psychiatric disease or disorder to be diagnosed with a psychiatric disease or disorder. A subject being treated or in need of treatment with one or more medications to alleviate one or more symptoms of a psychiatric disease or disorder is also referred to herein as a "psychiatric patient". In one embodiment, the subject is a psychiatric patient diagnosed with a psychiatric disease or disorder. In one embodiment, the subject is a psychiatric patient already undergoing treatment for a psychiatric disease or disorder which comprises administering one or more antipsychotic medications and the treatment is revised according to the methods of the present invention. In another embodiment, the subject has not yet begun treatment for a psychiatric disease or disorder and the subject is treated with one or more antipsychotic medications according to the methods of the present invention.

In one embodiment, the psychiatric disease or disorder is selected from the group consisting of schizophrenia and schizoaffective disorders. In one embodiment, the psychiatric disease or disorder is bipolar disorder. In one embodiment, the psychiatric disease or disorder is selected from a conduct disorder. In one embodiment, the psychiatric disease or disorder is autism or an autism spectrum disorder. In one embodiment, the psychiatric disease or disorder is attention deficit hyperactivity disorder (ADHD). In one embodiment, the psychiatric disease or disorder is depression.

In one embodiment, the invention provides methods for altering an existing treatment regimen or designing an initial treatment regimen for a subject in need of treatment with one or more antipsychotic medications, the method comprising determining the set of antipsychotic medications to be administered to the subject as well as the set of antipsychotic medications that should not be administered to the subject based upon the subject's AIWG risk assessment. In one embodiment, the methods further comprise the step of administering one or more antipsychotic medications to the subject.

In one embodiment, the methods of the invention comprise determining a subject's genotype at one or more SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6922310 (SEQ ID NO: 4) (HCRTR2^3), rs2653350 (SEQ ID NO: 5) (HCRTR2^4), rs6435326 (SEQ ID NO: 6) (NDUFS1), rs1053517 (SEQ ID NO: 7) (NDUFS1^1), rs 1801318 (SEQ ID NO: 8) (NDUFS1^2), rs6971 (SEQ ID NO: 9) (TSPO), and rs279858 (SEQ ID NO: 14) (GABRA2).

In one embodiment, the methods of the invention comprise determining or receiving a subject's genotype for at least one SNP selected from the group consisting of rs13429709 (SEQ ID NO: 1) (GCG), rs3134701 (SEQ ID NO: 2) (HCRTR2), rs4142972 (SEQ ID NO: 3)

(HCRTR2^2), rs6435326 (SEQ ID NO: 6) (NDUFS1), rs6971 (SEQ ID NO: 9) (TSPO), and rs279858 (SEQ ID NO: 14) (GABRA2). The GABRA2 polymorphism is described in Applicant's U.S. Provisional Application Ser. No. 61/892,094, filed on Oct. 17, 2013, the contents of which are hereby incorporated by reference.

In one embodiment, the methods of the invention comprise determining or receiving a subject's genotype for a panel of SNPs comprising at least two SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2).

In one embodiment, the methods of the invention comprise determining or receiving a subject's genotype for a panel of SNPs comprising at least three SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO).

In one embodiment, the methods of the invention comprise determining or receiving a subject's genotype for a panel of SNPs comprising at least four SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO).

In one embodiment, the methods of the invention comprise determining or receiving a subject's genotype for a panel of SNPs comprising at least five SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), and rs6971 (SEQ ID NO: 9) (TSPO).

In one embodiment, the methods of the invention comprise determining or receiving a subject's genotype for a panel of SNPs comprising at least six SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2).

In one embodiment, the methods of the invention comprise determining or receiving a subject's genotype for a panel of SNPs that includes at least one of rs3134701 (SEQ ID NO: 2) (HCRTR2) and rs4142972 (SEQ ID NO: 3) (HCRTR2^2). In one embodiment, the methods of the invention comprise determining or receiving a subject's genotype for a panel of SNPs that includes at least rs3134701 (SEQ ID NO: 2) (HCRTR2) and rs4142972 (SEQ ID NO: 3) (HCRTR2^2). In one embodiment, the panel of SNPs also includes one, two, or three, additional SNPs selected from the group consisting of rs13429709 (SEQ ID NO: 1) (GCG), rs6435326 (SEQ ID NO: 6) (NDUFS1), and rs6971 (SEQ ID NO: 9) (TSPO).

In one embodiment, the methods of the invention further comprise determining or receiving the subject's genotype at one or more additional SNPs selected from the group consisting of rs489693 (MC4R, see e.g., Malhotra et al., Arch Gen Psychiatry 69:904-912, 2012), rs16147 (NPY, see e.g., Tiwari et al., J Clin Psychopharmacology 33:11-17, 2013), and rs806378 (CNR1, see e.g., Tiwari et al., Neuropsychopharmacology 35:1315-1324, 2010). In one embodiment, the methods of the invention further comprise determining or receiving a subject's genotype for at least one additional SNP selected from the group consisting of rs2268639 (SEQ ID NO: 10) (GLPR1), rs489693 (SEQ ID NO: 11) (MC4R), rs806378 (SEQ ID NO: 12) (CNR1), and rs16147 (SEQ ID NO: 13) (NPY). In one embodiment, the at least one additional SNP is rs489693 (SEQ ID NO: 11) (MC4R).

In one embodiment, the methods of the invention further comprise identifying the number of risk genotypes the subject carries and, optionally, assigning a risk score to each genotype. In this context, a risk genotype includes information about whether, and in certain embodiments, how (e.g., dominant or recessive) each allele of the genotype is significantly associated with an increased risk of AIWG. Thus, in the context of the present invention, the term "risk allele" refers to an allele of an SNP identified as being associated with an increased risk of clinically significant weight gain in a subject being treated with one or more antipsychotic medications. In certain embodiments, a particular allele is further classified as a dominant or recessive allele with respect to AIWG. Each "risk genotype" of an SNP is further assigned a risk score based upon whether or not the genotype contains a risk allele and further based upon whether or not the risk allele is dominant or recessive. Risk alleles and associated genotypes for particular SNPs are indicated in Table 1.

Throughout this disclosure, SNPs are referred to by their "rs" number as well as a reference sequence (see Table 3 for SNP reference sequences and their sequence identifiers as used herein). The reference sequence shows the single nucleotide polymorphism in bold. The "rs" number for a given SNP is a reference number provided by the HapMap consortium. The rs number is sufficient to obtain much of the known information regarding a particular SNP, for example by querying the rs number in the HapMap database or similar databases including the UCSC Genome Bioinformatics Web Page and similar databases maintained by the US National Center for Biotechnology Information.

Risk Model for AIWG

The AIWG risk model of the invention incorporates information about a subject's genotype at one or more SNPs, preferably a subject's genotype for at least 5, at least 6, or at least 7 SNPs, and provides an output in the form of an AIWG risk assessment indicating the likelihood that the subject will experience a clinically significant weight gain while undergoing treatment with an antipsychotic agent, in particular an antipsychotic agent having a tendency to induce weight gain. Antipsychotic agents having a tendency to induce weight gain include medications such as risperidone, paliperidone and quetiapine, which have an intermediate risk of inducing weight gain, as well as clozapine and olanzapine, which have a high risk of inducing weight gain. Antipsychotic agents having a low risk of inducing weight gain include haloperidol, perphenazine, thioridazine, ziprasidone, aripiprazole, chlorpromazine, amisulpride, fluphenazine, molindone, loxapine, iloperidone, asenapine, and lurasidone.

In one embodiment, the AIWG risk assessment is qualitative, e.g., high, intermediate, low. In another embodiment, the AIWG risk assessment is a numerical value. The AIWG risk assessment incorporates the subject's total genetic risk score for one or more SNP's included in the model. The total genetic risk score is the sum of the individual risk scores for each genotype of each SNPs included in the model. The individual risk score for each genotype incorporates information regarding the contribution of each allele in the genotype to AIWG, as determined by the present invention. For example, the individual risk score includes information regarding the mode of inheritance (dominant or recessive) of the allele. In one embodiment, the numerical value for a genotype's risk score ranges from 0 (no risk of clinically significant weight gain) to 1 (highest risk of clinically significant weight gain). Table 1 lists the genotypes and risk scores for a set of SNPs that the inventors have determined are significantly associated with antipsychotic medication-induced weight gain and which may be incorporated individually or in panels of two or more into the risk model of the invention. Table 2 shows exemplary, but non-limiting, panels of SNPs for incorporation into a risk model as described herein.

In one embodiment, the model includes 2 SNPs and the AIWG risk assessment is high if the subject has a total genetic risk score of at least 2, intermediate if the subject has a total genetic risk score of 1 or more, but less than 2, and low if the subject has a total genetic risk score of less than 1, for example, 0.

In one embodiment, the model includes 3 SNPs and the AIWG risk assessment is high if the subject has a total genetic risk score of at least 3, intermediate if the total genetic risk score is between 1 and 3, for example, 2, and low if the subject has a total genetic risk score of less than 2, for example, 0 or 1.

In one embodiment, the model includes 4 or 5 SNPs and the AIWG risk assessment is high if the subject has a total genetic risk score of at least 4, intermediate if the total genetic risk score is less than 4 but greater than 1, for example, 2 or 3, and low if the subject has a total genetic risk score of less than 2, for example, 0 or 1.

In one embodiment, the model includes 6, 7, or 8 SNPs and the AIWG risk assessment is high if the subject has a total genetic risk score of at least 6, intermediate if the total genetic risk score is less than 6 but greater than 3, and low if the subject has a total genetic risk score of 3 or less. In another embodiment, the model includes 6, 7, or 8 SNPs and the AIWG risk assessment is high if the subject has a total genetic risk score of at least 5, intermediate if the total genetic risk score is less than 5 but at least 2, and low if the subject has a total genetic risk score of less than 2.

In one embodiment, the model may incorporate other relevant information into the AIWG risk assessment. For example, the model may incorporate information regarding the subject's ethnicity, duration of disease, baseline severity of disease, duration of treatment, medication dose, baseline weight, age, and gender. In one embodiment, the AIWG risk assessment incorporates information regarding the subject's ethnicity.

In one embodiment, the model determines the risk assessment cutoffs for the total genetic risk score based upon the panel of SNPs included in the model and the expected percentage weight change for the panel. In one embodiment, a total genetic risk score associated with an expected percentage weight change of less than 4% represents a low risk, a total genetic risk score associated with an expected percentage weight change of between 4% and 7% represents an intermediate risk, and a total genetic risk score associated with an expected percentage weight change of more than 7% represents a high risk. In one embodiment, an expected percentage weight change of 7% to 10% represents a high risk and more than 10% represents a very high risk.

As discussed in the following sections, the AIWG risk assessment is used in methods to improve therapeutic outcomes by preventing or reducing weight gain in a psychiatric patient being treated with one or more antipsychotic medications; for selecting an antipsychotic medication for a psychiatric patient that minimizes the patient's risk of clinically significant weight gain induced by the medication; reduce a psychiatric patient's risk of clinically significant weight gain induced by an antipsychotic medication; and for determining a psychiatric patient's susceptibility to weight gain by identifying at-risk patients and providing an assessment of that risk. The AIWG risk assessment is also used in methods for designing a therapeutic regimen for a patient that minimizes the risk of weight gain. The methods may also include generating and outputting a patient-specific report identifying the patient according to the patient's particular risk of clinically significant weight gain induced by an antipsychotic medication, providing an assessment of that risk, and including a list of medications categorized according to the relative risk of weight gain presented by each for the patient.

Risk Markers and Alleles for AIWG

The present invention provides a number of risk alleles for AIWG, as shown in Table 1 below.

TABLE 1

Genetic Markers Associated with Antipsychotic Medication-Induced Weight Gain

| SNP (human) | Gene (human) | Allele/Effect | Genotype/Risk Score |
|---|---|---|---|
| rs13429709 SEQ ID NO: 1 | GCG | C - dominant | CC - high, 1<br>CT - high, 1<br>TT - low, 0 |
| rs3134701 SEQ ID NO: 2 | HCRTR2 | A - recessive | AA - high, 1<br>AG - low, 0<br>GG - low, 0 |
| rs4142972 SEQ ID NO: 3 | HCRTR2 | A - dominant | AA - high, 1<br>AG - high, 1<br>GG - low, 0 |
| rs6922310 SEQ ID NO: 4 | HCRTR2 | A - recessive | AA - high, 1<br>AG - low, 0<br>GG - low, 0 |
| rs2653350 SEQ ID NO: 5 | HCRTR2 | A - recessive | AA - high, 1<br>AG - low, 0<br>GG - low, 0 |
| rs6435326 SEQ ID NO: 6 | NDUFS1 | A - recessive | AA - high, 1<br>AT - low, 0<br>TT - low, 0 |
| rs6971 SEQ ID NO: 9 | TSPO | A - dominant | AA - high, 1<br>AG - high, 1<br>GG - low, 0 |
| rs489693 SEQ ID NO: 11 | MC4R | A - recessive | AA - high, 1<br>AC - low, 0<br>CC - low, 0 |
| rs806378 SEQ ID NO: 12 | CNR1 | T - dominant | TT - high, 1<br>CT - high, 1<br>CC - low, 0 |
| rs16147 SEQ ID NO: 13 | NPY | G - dominant | GG - high, 1<br>GA - high, 1<br>AA - low, 0 |
| rs279858 SEQ ID NO: 14 | GABRA2 | T - recessive | TT - high, 1<br>TC - high, 1<br>CC - low, 0 |

TABLE 2

Exemplary Panels of Genetic Markers Associated with Antipsychotic Medication-Induced Weight Gain

| Panel # | SNPs (human) | Genes (human) | Genotype | Risk Score |
|---|---|---|---|---|
| 1 | rs3134701 | HCRTR2 | AA | 1 |
| | | | AG | 0 |
| | | | GG | 0 |
| | rs4142972 | HCRTR2 | AA | 1 |
| | | | AG | 1 |
| | | | GG | 0 |

TABLE 2-continued

Exemplary Panels of Genetic Markers Associated with Antipsychotic Medication-Induced Weight Gain

| Panel # | SNPs (human) | Genes (human) | Genotype | Risk Score |
|---|---|---|---|---|
| 2 | rs3134701 | HCRTR2 | AA | 1 |
|  |  |  | AG | 0 |
|  |  |  | GG | 0 |
|  | rs13429709 | GCG | CC | 1 |
|  |  |  | CT | 1 |
|  |  |  | TT | 0 |
| 3 | rs3134701 | HCRTR2 | AA | 1 |
|  |  |  | AG | 0 |
|  |  |  | GG | 0 |
|  | rs6971 | TSPO | AA | 1 |
|  |  |  | AG | 1 |
|  |  |  | GG | 0 |
| 4 | rs3134701 | HCRTR2 | AA | 1 |
|  |  |  | AG | 0 |
|  |  |  | GG | 0 |
|  | rs6435326 | NDUFS1 | AA | 1 |
|  |  |  | AT | 0 |
|  |  |  | TT | 0 |
| 5 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs13429709 | GCG | CC | 1 |
|  |  |  | CT | 1 |
|  |  |  | TT | 0 |
| 6 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs6971 | TSPO | AA | 1 |
|  |  |  | AG | 1 |
|  |  |  | GG | 0 |
| 7 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs6435326 | NDUFS1 | AA | 1 |
|  |  |  | AT | 0 |
|  |  |  | TT | 0 |
| 8 | rs3134701 | HCRTR2 | AA | 1 |
|  |  |  | AG | 0 |
|  |  |  | GG | 0 |
|  | rs13429709 | GCG | CC | 1 |
|  |  |  | CT | 1 |
|  |  |  | TT | 0 |
|  | rs6971 | TSPO | AA | 1 |
|  |  |  | AG | 1 |
|  |  |  | GG | 0 |
| 9 | rs4142972 | HCRTR2 | AA | 1 |
|  |  |  | AG | 1 |
|  |  |  | GG | 0 |
|  | rs13429709 | GCG | CC | 1 |
|  |  |  | CT | 1 |
|  |  |  | TT | 0 |
|  | rs6435326 | NDUFS1 | AA | 1 |
|  |  |  | AT | 0 |
|  |  |  | TT | 0 |
| 10 | rs4142972 | HCRTR2 | AA | 1 |
|  |  |  | AG | 1 |
|  |  |  | GG | 0 |
|  | rs6971 | TSPO | AA | 1 |
|  |  |  | AG | 1 |
|  |  |  | GG | 0 |
|  | rs6435326 | NDUFS1 | AA | 1 |
|  |  |  | AT | 0 |
|  |  |  | TT | 0 |
| 11 | rs3134701 | HCRTR2 | AA | 1 |
|  |  |  | AG | 0 |
|  |  |  | GG | 0 |
|  | rs13429709 | GCG | CC | 1 |
|  |  |  | CT | 1 |
|  |  |  | TT | 0 |
|  | rs6971 | TSPO | AA | 1 |
|  |  |  | AG | 1 |
|  |  |  | GG | 0 |
|  | rs6435326 | NDUFS1 | AA | 1 |
|  |  |  | AT | 0 |
|  |  |  | TT | 0 |
| 12 | rs4142972 | HCRTR2 | AA | 1 |
|  |  |  | AG | 1 |
|  |  |  | GG | 0 |
|  | rs13429709 | GCG | CC | 1 |
|  |  |  | CT | 1 |
|  |  |  | TT | 0 |
|  | rs6971 | TSPO | AA | 1 |
|  |  |  | AG | 1 |
|  |  |  | GG | 0 |
|  | rs6435326 | NDUFS1 | AA | 1 |
|  |  |  | AT | 0 |
|  |  |  | TT | 0 |
| 13 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs13429709 | GCG | CC | 1 |
|  |  |  | CT | 1 |
|  |  |  | TT | 0 |
|  | rs6971 | TSPO | AA | 1 |
|  |  |  | AG | 1 |
|  |  |  | GG | 0 |
| 14 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs13429709 | GCG | CC | 1 |
|  |  |  | CT | 1 |
|  |  |  | TT | 0 |
|  | rs6435326 | NDUFS1 | AA | 1 |
|  |  |  | AT | 0 |
|  |  |  | TT | 0 |
| 15 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs6971 | TSPO | AA | 1 |
|  |  |  | AG | 1 |
|  |  |  | GG | 0 |
|  | rs6435326 | NDUFS1 | AA | 1 |
|  |  |  | AT | 0 |
|  |  |  | TT | 0 |
| 16 | rs3134701 | HCRTR2 | AA | 1 |
|  |  |  | AG | 0 |
|  |  |  | GG | 0 |
|  | rs4142972 | HCRTR2 | AA | 1 |
|  |  |  | AG | 1 |
|  |  |  | GG | 0 |
|  | rs6971 | TSPO | AA | 1 |
|  |  |  | AG | 1 |
|  |  |  | GG | 0 |

TABLE 2-continued

Exemplary Panels of Genetic Markers Associated with Antipsychotic Medication-Induced Weight Gain

| Panel # | SNPs (human) | Genes (human) | Genotype | Risk Score |
|---|---|---|---|---|
| | rs6435326 | NDUFS1 | AA | 1 |
| | | | AT | 0 |
| | | | TT | 0 |
| | rs13429709 | GCG | CC | 1 |
| | | | CT | 1 |
| | | | TT | 0 |
| 17 | rs3134701 | HCRTR2 | AA | 1 |
| | | | AG | 0 |
| | | | GG | 0 |
| | rs4142972 | HCRTR2 | AA | 1 |
| | | | AG | 1 |
| | | | GG | 0 |
| | rs6971 | TSPO | AA | 1 |
| | | | AG | 1 |
| | | | GG | 0 |
| | rs6435326 | NDUFS1 | AA | 1 |
| | | | AT | 0 |
| | | | TT | 0 |
| | rs13429709 | GCG | CC | 1 |
| | | | CT | 1 |
| | | | TT | 0 |
| | rs806378 | CNR1 | TT | 1 |
| | | | CT | 1 |
| | | | CC | 0 |
| 18 | rs3134701 | HCRTR2 | AA | 1 |
| | | | AG | 0 |
| | | | GG | 0 |
| | rs4142972 | HCRTR2 | AA | 1 |
| | | | AG | 1 |
| | | | GG | 0 |
| | rs6971 | TSPO | AA | 1 |
| | | | AG | 1 |
| | | | GG | 0 |
| | rs6435326 | NDUFS1 | AA | 1 |
| | | | AT | 0 |
| | | | TT | 0 |
| | rs13429709 | GCG | CC | 1 |
| | | | CT | 1 |
| | | | TT | 0 |
| | rs806378 | CNR1 | TT | 1 |
| | | | CT | 1 |
| | | | CC | 0 |
| | rs16147 | NPY | GG | 1 |
| | | | GA | 1 |
| | | | AA | 0 |
| 19 | rs3134701 | HCRTR2 | AA | 1 |
| | | | AG | 0 |
| | | | GG | 0 |
| | rs4142972 | HCRTR2 | AA | 1 |
| | | | AG | 1 |
| | | | GG | 0 |
| | rs6971 | TSPO | AA | 1 |
| | | | AG | 1 |
| | | | GG | 0 |
| | rs6435326 | NDUFS1 | AA | 1 |
| | | | AT | 0 |
| | | | TT | 0 |
| | rs13429709 | GCG | CC | 1 |
| | | | CT | 1 |
| | | | TT | 0 |
| | rs806378 | CNR1 | TT | 1 |
| | | | CT | 1 |
| | | | CC | 0 |
| | rs16147 | NPY | GG | 1 |
| | | | GA | 1 |
| | | | AA | 0 |
| | rs489693 | MC4R | AA | 1 |
| | | | AC | 0 |
| | | | CC | 0 |
| 20 | rs13429709 | GCG | CC | 1 |
| | | | CT | 1 |
| | | | TT | 0 |
| | rs3134701 | HCRTR2 | AA | 1 |
| | | | AG | 0 |
| | | | GG | 0 |
| | rs4142972 | HCRTR2 | AA | 1 |
| | | | AG | 1 |
| | | | GG | 0 |
| | rs6971 | TSPO | AA | 1 |
| | | | AG | 1 |
| | | | GG | 0 |
| | rs6435326 | NDUFS1 | AA | 1 |
| | | | AT | 0 |
| | | | TT | 0 |
| | rs279858 | GABRA2 | TT | 1 |
| | | | TC | 1 |
| | | | CC | 0 |
| 21 | rs13429709 | GCG | CC | 1 |
| | | | CT | 1 |
| | | | TT | 0 |
| | rs3134701 | HCRTR2 | AA | 1 |
| | | | AG | 0 |
| | | | GG | 0 |
| | rs4142972 | HCRTR2 | AA | 1 |
| | | | AG | 1 |
| | | | GG | 0 |
| | rs6435326 | NDUFS1 | AA | 1 |
| | | | AT | 0 |
| | | | TT | 0 |
| | rs489693 | MC4R | AA | 1 |
| | | | AC | 0 |
| | | | CC | 0 |
| | rs806378 | CNR1 | TT | 1 |
| | | | CT | 1 |
| | | | CC | 0 |
| | rs16147 | NPY | GG | 1 |
| | | | GA | 1 |
| | | | AA | 0 |

TABLE 3

SNP Reference Sequences

| SNP (human) | Gene (human) | Sequence |
|---|---|---|
| rs13429709 SEQ ID NO: 1 | GCG | GGCTGATGCCTCACTGTGTGTGTCC[C/T]GAGATGTTCTCAAGGTTTTGACTTT |
| rs3134701 SEQ ID NO: 2 | HCRTR2 | TGATGAACAACAGAAATTTGTTTCC[A/G]ACTGTTTTGGAGACTGGGAAGTCCA |
| rs4142972 SEQ ID NO: 3 | HCRTR2 | AGCATTCATGAACAAATTCCTGTGC[A/G]AAGATTGAGAATGAAAGATGAATAA |
| rs6922310 SEQ ID NO: 4 | HCRTR2 | ACATGCCCAGCTTCAGAAATGAGTC[A/G]TGATTTTCTAAAGCAACAATATCA |
| rs2653350 SEQ ID NO: 5 | HCRTR2 | TCTCCTTAAAACTTAACTTTTTGCC[A/G]AATTAGTCAAAGCAATTTCTTTAC |
| rs6435326 SEQ ID NO: 6 | NDUFS1 | GGAATAACTCCTTTTGTAATAAAGA[A/T]AGATTTAAATGAAGTTAAAAGTGCA |

TABLE 3 -continued

SNP Reference Sequences

| SNP (human) | Gene (human) | Sequence |
|---|---|---|
| rs1053517 SEQ ID NO: 7 | NDUFS1 | ATAAGGTTTTAGAATAATAGTATGT[C/T]ACAATATCTTTAAAAACAGCAGGTG |
| rs1801318 SEQ ID NO: 8 | NDUFS1 | TTGAGGCACCACTGTTTAATGCTAG[A/G]ATTCGAAAGAGGTTGGTAATAGTAT |
| rs6971 SEQ ID NO: 9 | TSPO | CATACGCAGTAGTTGAGTGTGGTCG[C/T]GAAGGCCAGCCAGGCCAGGTAGGGG |
| rs2268639 SEQ ID NO: 10 | GLPR1 | TGAGAAACGGGGACGTGGGGGGGTC[A/T]AGATGACAAGGTGGCAGCAGGGAGC |
| rs489693 SEQ ID NO: 11 | MC4R | TCTTAATTCTGTTGTCATTAGTTCC[A/C]GTTTGTTAAATGTTTACAGCGTGGC |
| rs806378 SEQ ID NO: 12 | CNR1 | CCCTCTATTACAGGCCTCATCACGT[C/T]GTATAATCAGGAGTTCACATATTTA |
| rs16147 SEQ ID NO: 13 | NPY | TTGTCTCCTGCCAACAGGACTACCA[A/G]CCCACTGGGTGCCGGAGTAGGAAGC |
| rs279858 SEQ ID NO: 14 | GABRA2 | ATTGTCATATTATGAGCTACTGATTT[T/C]TTCCCATTGTGAAAAAGGTATCTG |

Methods of Administering and Treating with Antipsychotic Medications to Reduce AIWG The methods of the invention provide for the treatment of a subject having a psychiatric disease or disorder based upon the subject's AIWG risk assessment as determined according to the invention. As discussed above, the AIWG risk assessment incorporates information about the subject's genotype at one or more SNPs, as provided herein. In one embodiment the AIWG risk assessment incorporates the subject's total genetic risk score, as provided herein, and optionally one or more additional patient-specific data attributes selected from the subject's ethnicity, duration of disease, baseline severity of disease, duration of treatment, medication dose, baseline weight, age, and gender.

The methods of the invention also provide for different treatments, or different treatment regimens, for the subject depending on the subject's AIWG risk assessment. Thus, the methods of the invention include methods for designing a treatment regimen, methods for selecting an antipsychotic medication for administration to a subject, and methods for determining a subject's susceptibility to AIWG, all using the subject's AIWG risk assessment, as provided herein.

In one embodiment, the methods of the invention are applicable to a subject regardless of the subject's ethnicity because risk alleles identified by the invention occur with similar frequencies among the major ethnic groups, as shown in the table below.

TABLE 4

Genotypic and allelic frequencies of the SNPs in different populations. CEU—European ancestry; HCB &JPT: Asian Ancestry and YRI: Sub-Saharan African ancestry.

| Gene | SNP | Genotype | CEU | HCB | JPT | YRI | Allele | CEU | HCB | JPT | YRI |
|---|---|---|---|---|---|---|---|---|---|---|---|
| CNR1 | rs806378 | CC | 0.55 | 0.578 | 0.682 | 0.917 | C | 0.742 | 0.767 | 0.841 | 0.958 |
| | | CT | 0.383 | 0.378 | 0.318 | 0.083 | T | 0.258 | 0.233 | 0.159 | 0.042 |
| | | TT | 0.067 | 0.044 | | | | | | | |
| NPY | rs16147 | AA | 0.283 | 0.14 | 0.105 | 0.398 | A | 0.491 | 0.36 | 0.314 | 0.615 |
| | | AG | 0.416 | 0.442 | 0.419 | 0.434 | G | 0.509 | 0.64 | 0.686 | 0.385 |
| | | GG | 0.301 | 0.419 | 0.477 | 0.168 | | | | | |
| GCG | rs13429709 | CC | 0.036 | 0.422 | 0.419 | 0.379 | C | 0.257 | 0.689 | 0.64 | 0.612 |
| | | CT | 0.441 | 0.533 | 0.442 | 0.466 | T | 0.743 | 0.311 | 0.36 | 0.388 |
| | | TT | 0.523 | 0.044 | 0.14 | 0.155 | | | | | |
| MC4R | rs489693 | AA | 0.167 | | 0.091 | 0.317 | A | 0.408 | 0.189 | 0.318 | 0.55 |
| | | AC | 0.483 | 0.378 | 0.455 | 0.467 | C | 0.592 | 0.811 | 0.682 | 0.45 |
| | | CC | 0.35 | 0.622 | 0.455 | 0.217 | | | | | |
| HCRTR2 | rs3134701 | AA | 0.633 | 0.614 | 0.5 | 0.322 | A | 0.808 | 0.761 | 0.726 | 0.568 |
| | | AG | 0.35 | 0.295 | 0.452 | 0.492 | G | 0.192 | 0.239 | 0.274 | 0.432 |
| | | GG | 0.017 | 0.091 | 0.048 | 0.186 | | | | | |
| | rs4142972 | AA | 0.018 | 0.07 | 0.058 | 0.018 | A | 0.128 | 0.337 | 0.25 | 0.146 |
| | | AG | 0.221 | 0.535 | 0.384 | 0.257 | G | 0.872 | 0.663 | 0.75 | 0.854 |
| | | GG | 0.761 | 0.395 | 0.558 | 0.726 | | | | | |
| TSPO | rs6971 | Ala/Ala (GG) | 0.513 | 0.977 | 0.93 | 0.788 | G | 0.708 | 0.988 | 0.965 | 0.894 |
| | | Ala/Thr (GA) | 0.389 | 0.023 | 0.07 | 0.212 | A | 0.292 | 0.012 | 0.035 | 0.106 |
| | | Thr/Thr (AA) | 0.097 | | | | | | | | |
| NDUFS1 | rs6435326 | AA | 0.233 | 0.556 | 0.591 | 0.15 | A | 0.508 | 0.744 | 0.784 | 0.342 |
| | | AT | 0.55 | 0.378 | 0.386 | 0.383 | T | 0.492 | 0.256 | 0.216 | 0.658 |
| | | TT | 0.217 | 0.067 | 0.023 | 0.467 | | | | | |

CEU—Utah residents with ancestry from Northern and Western European (CEPH collection)
CHB—Han Chinese in Beijing, China
JPT—Japanese Tokyo
YRI—Yoruba in Ibadan, Nigeria In one embodiment, the methods of the invention provide for the treatment of a subject in need of treatment for a psychiatric disease or disorder, the methods comprising administering an antipsychotic medication to the subject based on the subject's AIWG risk assessment such that antipsychotic medications having a high tendency to induce weight gain are avoided in favor of those having a low or intermediate tendency to induce weight gain. In one embodiment, where the subject has a high AIWG risk assessment, the method comprises administering one or more antipsychotic medications selected from the group consisting of haloperidol, perphenazine, thioridazine, ziprasidone, aripiprazole, chlorpromazine, amisulpride, fluphenazine, molindone, loxapine, paliperidone, iloperidone, asenapine, and lurasidone, or administering risperidone or quetiapine in combination with weight monitoring, and avoiding clozapine and olanzapine.

In the context of the methods of the invention, weight monitoring means the periodic determination of the subject's weight during treatment. For example, the weight monitoring may include determining the subject's weight every two weeks for the first three to six months of treatment, then on a monthly basis. Weight monitoring is used to monitor any weight gain by the subject during treatment. For example, if the subject gains weight initially, and continues to gain weight such that the subject is on a course to gain 7% or more relative to the subject's baseline weight (the subject's weight at the start of treatment), the clinician should consider changing the subject's treatment regimen either to substitute the subject's antipsychotic medication for one having a lower tendency to induce weight gain, and/or adding to the regimen additional elements to mitigate weight gain, such as diet and exercise.

In one embodiment, where the AIWG risk assessment is intermediate, the methods comprise administering one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or administering clozapine or olanzapine in combination with weight monitoring.

In one embodiment, where the AIWG risk assessment is low, the methods comprise administering one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic.

In one embodiment, the methods of the invention provide for selecting an antipsychotic medication for a subject in need of treatment for a psychiatric disease or disorder, the methods comprising selecting an antipsychotic medication based on the subject's AIWG risk assessment such that antipsychotic medications having a high tendency to induce weight gain are avoided in favor of those having a low or intermediate tendency to induce weight gain. In one embodiment, where the subject has a high AIWG risk assessment, the method comprises selecting one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or selecting risperidone, paliperidone, or quetiapine in combination with weight monitoring, and avoiding clozapine and olanzapine. In one embodiment, where the AIWG risk assessment is intermediate, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or selecting clozapine or olanzapine in combination with weight monitoring. In one embodiment, where the AIWG risk assessment is low, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic.

In one embodiment, the methods of the invention provide for determining a subject's susceptibility to antipsychotic medication induced weight gain based on the subject's AIWG risk assessment. In one embodiment, where the subject has a high AIWG risk assessment, the subject's susceptibility is determined to be high and the method comprises recommending for the subject one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or recommending risperidone, paliperidone, or quetiapine in combination with weight monitoring, and recommending that the subject avoid clozapine and olanzapine. In one embodiment, where the AIWG risk assessment is intermediate, the subject's susceptibility is determined to be intermediate and the methods comprise recommending for the subject one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or recommending clozapine or olanzapine in combination with weight monitoring. In one embodiment, where the AIWG risk assessment is low, the subject's susceptibility is determined to be low and the methods comprise recommending for the subject one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic.

In one embodiment, the methods of the invention provide for designing a therapeutic regimen for a subject in need of treatment with an antipsychotic medication, the methods comprising selecting an antipsychotic medication based on the subject's AIWG risk assessment such that antipsychotic medications having a high tendency to induce weight gain are avoided in favor of those having a low or intermediate tendency to induce weight gain. In one embodiment, where the subject has a high AIWG risk assessment, the method comprises selecting one or more antipsychotic medications selected from the group consisting of haloperidol, perphenazine, thioridazine, ziprasidone, aripiprazole, chlorpromazine, amisulpride, fluphenazine, molindone, loxapine, iloperidone, asenapine, and lurasidone, or selecting risperidone, paliperidone, or quetiapine in combination with weight monitoring, and avoiding clozapine and olanzapine. In one embodiment, where the AIWG risk assessment is intermediate, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or selecting clozapine or olanzapine in combination with weight monitoring. In one embodiment, where the AIWG risk assessment is low, the methods comprise selecting one or more antipsychotic medications selected from the group consisting of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, olanzapine, and any other weight neutral antipsychotic. In embodiments where weight monitoring forms part of the therapeutic regimen, additional elements such as diet and exercise may be added to the regimen to mitigate weight gain.

In one embodiment, the methods of the invention further comprise one or more additional steps selected from the group consisting of (1) testing the subject for one or more additional genetic markers, (2) advising and/or counseling the subject with respect to the results of an AIWG risk assessment, (3) transmitting, advising and/or conveying the results of an AIWG risk assessment to a physician, medical service provider or other third party, (4) altering the subject's treatment regimen based on the results of an AIWG risk assessment in order to lower the subjects risk of weight gain, (5) treating the subject prior to, concurrently with or after antipsychotic treatment with one or more therapies to control weight gain, for example, administering to the subject an appetite suppressant or hypoglycemic medication selected from the group consisting of a sulfonylurea, thiazolidinedione, alpha glucosidase inhibitor, and metformin, (6) monitoring the subject's weight over a period of time, (7) monitoring the subject for metabolic syndrome or the development of metabolic syndrome which may include measuring one or more of blood lipid profiles, including triglycerol and triglycerides, blood glucose levels, body mass index (BMI) and central obesity, and (8) monitoring the subject for the development of heart disease as indicated for example by elevated blood pressure, angina, heart failure, shortness of breath, rapid or irregular pulse, coughing and nausea, or any combination of the above.

In one embodiment, the subject presents with one or more psychotic symptoms, schizophrenia symptoms, schizoaffective disorder symptoms or a combination thereof. The psychotic symptoms may comprise positive symptoms such as, but not limited to distortions or exaggerations of inferential thinking (i.e. delusions), perception (i.e. hallucinations), language and communication (disorganized speech) and behavioral monitoring (grossly disorganized or catatonic behavior) or any combination thereof. Further, the positive symptoms may comprise distinct dimensions, for example, psychotic dimensions including, but not limited to delusions and hallucinations and disorganization dimensions including, but not limited to disorganized speech and behavior. The symptoms may also comprise one or more negative symptoms, for example, but not limited to symptoms that reflect a diminution or loss of normal function (including but not limited to, loss of motivation, loss of social interest, loss of communication, or a combination thereof). Further, the subject may exhibit a combination of both positive and negative symptoms. In an embodiment of the invention, the subject has been diagnosed or is suspected of having schizophrenia or schizoaffective disorder on the basis of the subject's having presented with one or more of the foregoing positive and negative psychotic symptoms.

In one embodiment, the subject presents with one or more symptoms selected from the group consisting of catatonia, depressed mood, severe obsessions and/or compulsions or psychomotor agitation. In one embodiment, the subject presents with one or more symptoms of mania, including but not limited to elevated, expansive or irritable mood, exaggerated goal-directed activity, inflated self-esteem or grandiosity and decreased need for sleep. In one embodiment, the subject presents with one or more symptoms of impulse-control, conduct or disruptive disorders including failure to control aggressive impulses, aggression to people/animals/property and serious violations of widely accepted rules. Further symptoms include disruptive behavior in neurodevelopmental disorders including but not limited to intellectual disability, autism and attention-deficit/hyperactivity disorder. In one embodiment, the subject presents with one or more symptoms of severe tic disorders including Tourette syndrome or with severe stereotypic movement disorders.

The genotype of the subject is determined by techniques known in the art, for example, PCR analysis, DNA sequencing, 5'exonuclease fluorescence assay, sequencing by probe hybridization, dot blotting, and oligonucleotide array (DNA Chip) hybridization analysis, or combinations thereof. Such techniques are described, for example, in Ausubel, et al. (eds), 1989, Current Protocols in Molecular Biology, Green Publishing Associates, Inc., and John Wiley & Sons, Inc., New York, at p. 2.10.3, and in Maniatis et al., in Molecular Cloning (A Laboratory Manual), Cold Spring Harbor Laboratory, 1982, p. 387 389). Real-time PCR methods that can be used to detect SNPs, include, e.g., Taqman or molecular beacon-based assays (U.S. Pat. Nos. 5,210,015; 5,487,972; and PCT WO 95/13399) are useful to monitor for the presence or absence of a SNP. Genotyping technology is commercially available, for example from companies such as Applied Biosystems, Inc (Foster City, Calif.). Any suitable biological sample from the subject can be used as the source of the DNA for genotyping.

Kits

The present invention also contemplates products and kits for practicing the methods of the present invention. In one embodiment, a kit provided by the invention comprises a set of primers adapted to amplify, in a polymerase chain reaction, at least one nucleotide sequence comprising a single nucleotide polymorphism (SNP) as defined in the SNPs selected from the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2). In one embodiment, the kit comprises a set of primers adapted to amplify, in a polymerase chain reaction, at least one nucleotide sequence comprising a single nucleotide polymorphism (SNP) as defined in the SNPs selected from the group consisting of rs3134701 (SEQ ID NO: 2) (HCRTR2) and rs4142972 (SEQ ID NO: 3) (HCRTR2^2). In one embodiment, the kit comprises a set of primers adapted to amplify at least one nucleotide sequence comprising a single nucleotide polymorphism (SNP) as defined in the SNPs selected from the group consisting of rs3134701 (SEQ ID NO: 2) (HCRTR2) and rs4142972 (SEQ ID NO: 3) (HCRTR2^2) and at least one additional set of primers adapted to amplify at least one nucleotide sequence comprising a single nucleotide polymorphism (SNP) as defined in the SNPs selected from the group consisting of rs13429709 (SEQ ID NO: 1) (GCG), rs6435326 (SEQ ID NO: 6) (NDUFS1), and rs6971 (SEQ ID NO: 9) (TSPO).

In one embodiment, a kit provided by the invention comprises one or more polynucleotide probes adapted to hybridize with at least one SNP defined in the group consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2). In one embodiment, the kit comprises one or more polynucleotide probes adapted to hybridize with at least one SNP defined in the group consisting of rs3134701 (SEQ ID NO: 2) (HCRTR2) and rs4142972 (SEQ ID NO: 3) (HCRTR2^2). In one embodiment, the kit comprises one or more polynucleotide probes adapted to hybridize with at least one SNP defined in the group consisting of rs3134701 (SEQ ID NO: 2) (HCRTR2) and rs4142972 (SEQ ID NO: 3) (HCRTR2^2) and the kit further comprises one or more additional polynucleotide probes adapted to hybridize with at least one SNP defined in the group consisting of rs13429709 (SEQ ID NO: 1) (GCG), rs6435326 (SEQ ID NO: 6) (NDUFS1), and rs6971 (SEQ ID NO: 9) (TSPO). In the context of this embodiment, the term "hybridize" refers to specific hybridization such as occurs between the probe and its complementary nucleotide sequence under high stringency hybridization conditions, as those conditions are understood in the art. In one embodiment, the probe is labeled with a detectable label, such as a radionuclide, a fluorescent molecule, a magnetic bead, or chemical entity, or any other suitable label that can be attached to or incorporated within a polynucleotide sequence. In one embodiment, the probe is attached covalently or physically associated with a support for example, but not limited to a biochip, array, slide, multiwell plate, bead or the like. In an embodiment, the probe comprises an array of nucleic acids attached or associated with a solid support.

The kits of the present invention may also optionally comprise one or more reagents and/or products including, but not limited to, one or more buffers for performing PCR or probe hybridization, or any step in such a process as would be known to a person of skill in the art, one or more DNA amplifying enzymes, or any combination thereof; one or more reagents, components and products for genotyping the polymorphisms as described herein, including, but not limited to those used in exonuclease assays, nucleotide sequencing, or any combination thereof; one or more reagents, components or products for performing a DNA sequencing reaction that determines the sequence of a nucleotide sequence of an SNP defined herein; a gene chip or array comprising one or a plurality of nucleotide sequences comprising or consisting of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2), and; one or more sets of instructions for using the components as described herein, practicing the methods of the present invention as described herein, interpreting the data obtained from practicing the methods of the present invention or; any combination or sub-combination thereof.

Also provided by the present invention are individual components of the kit, for example, but not limited to any product, composition described in the kit or elsewhere in the application. In a representative embodiment, the present invention provides one or more nucleic acid primers or probes.

The nucleic acid primers and probes may be of any suitable length for use in the method of the present invention. Without wishing to be limiting in any manner, it is generally preferred that the primers and probes be between about 9 and about 100 nucleotides, for example, but not limited to about 7, 8, 9, 10, 11, 12, 13, 14, 15, 16, 17, 18, 19, 20, 21, 23, 25, 27, 29, 30, 35, 40, 45, 50, 60, 70, 80, 90, about 100 nucleotides or any amount therein between. The length of the primers and probes may also be defined by a range of any two of the values provided above or any two values therein between. With respect to probes, it is generally preferred that the probe comprise at least one, more preferably 3 or more nucleotides on each side of the polymorphic site. It is also contemplated that one or more of the primers or nucleic acid probes may be labeled as is known in the art, for example, but not limited to, with a radioactive element or tag, fluorophore, or the like.

Also provided by the present invention is a microanay, gene chip or the like which comprises the nucleotide sequence defined by any one or more of rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2), or a fragment thereof which comprises the polymorphic site. Preferably the microarray or gene chip comprises nucleotide sequences defined by at least rs3134701 (SEQ ID NO: 2) (HCRTR2), rs4142972 (SEQ ID NO: 3) (HCRTR2^2) and optionally further comprising nucleotide sequences defined by one or more of rs13429709 (SEQ ID NO: 1) (GCG), rs6435326 (SEQ ID NO: 6) (NDUFS1), and rs6971 (SEQ ID NO: 9) (TSPO). The microanay also may comprise the complement of the nucleotide sequences or a fragment thereof which comprises the polymorphic site. Preferably, the nucleotide sequences are of a length such as, but not limited to 7, 8, 9, 10, 11, 12, 13, 14, 15, 16, 17, 18, 19, 20, 21, 22, 23, 24, 25 or more continuous nucleotides to permit strong hybridization under stringent hybridization conditions. In a preferred embodiment the microarray comprises or consists of one or more nucleotide sequences comprising the polymorphic sites in rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1), rs6971 (SEQ ID NO: 9) (TSPO), and rs279858 (SEQ ID NO: 14) (GABRA2), as described herein. However, the microarray may comprise additional nucleotide sequences for other genes, for example, but not limited to those involved or implicated in the diagnosis or development of schizophrenia, schizoaffective disorder or the like.

System

FIG. 1 illustrates an example of a system that can implement one or more features described herein. Here, system 100 includes a processor 110 and a memory 120. In some embodiments, memory 120 can include executable instructions that when executed by processor 110, cause the processor 110 to perform one or more operations discussed herein. System 100 also includes a user interface 160 which permits the system to interact with a user through, for example, one or more input devices 170 and one or more displays 175.

System 100 can also include one or more modules and/or engines that implement one or more features described herein. For example, system 100 can include Genetic Risk Score Generator 130, which can, for example, generate a total genetic risk score for a subject representing the risk of weight gain associated with the subject's genotype. System 100 can also include AIWG Risk Assessment Generator 140 which can, for example, generate an AIWG risk assessment for the subject using one or more data attributes including the subject's total genetic risk score. Moreover, system 110 can include Antipsychotic Medication Selection Engine 150, which can, for example, select an antipsychotic medication for the subject based on the subject's AIWG risk assessment.

In some embodiments, system 100 can be configured to receive a patient's data from a genotype determining equipment 180. In some embodiments, one or more patient data can be stored in a data storage or database 190 which is connected to the system via a data connection.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, modules, model generators, computer instructions, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The present invention will be further illustrated in the following examples.

EXAMPLES

1. Genetic Markers Near GCG

A total of N=128 schizophrenia or schizoaffective disorder subjects were included in the study (for detailed description of the samples, see Tiwari et al. 2010; Tiwari et al. 2010; Brandl et al. 2012; Brandl et al. 2013; Tiwari et al. 2013). Diagnosis was made according to DSM-III-R or DSM-IV criteria. Subjects were recruited from two different sites: Sample A (N=74; HYM) was collected at Case Western Reserve University, Cleveland, Ohio, USA. Patients were naïve to second-generation antipsychotics and received clozapine for six weeks. Sample B (N=54; JAL) was collected at Hillside Hospital in Glen Oaks, N.Y., USA. Patients were treated with clozapine, risperidone, olanzapine or haloperidol using a double-blind study design. Prior to study entry, written informed consent was obtained from all subjects according to institutional ethics guidelines. Detailed demographic and clinical characteristics are provided in Table 5 and have been published previously (Tiwari et al. 2010; Tiwari et al. 2013).

Single nucleotide polymorphisms (SNPs) in or near GCG and GLP1R were selected using the hapmap database (http://hapmap.ncbi.nlm.nih.gov/) based on linkage disequilibrium (LD), conservation and region (10 kb upstream and 2 kb downstream of the genes). A total of four SNPs in the GCG region (rs1990761, rs41368446, rs13429709, rs3761656) were selected. All SNPs were located near the gene due to very low minor allele frequency of variants in the gene. For GLP1R, we selected a total of 33 SNPs in and near the gene (rs9296291, rs10305456, rs10305432, rs13202369, rs910166, rs12528717, rs2300616, rs10305439, rs10305491, rs926674, rs2254336, rs1126476, rs1042044, rs6923761, rs2206942, rs2268640, rs9283907, rs932443, rs4714210, rs2268646, rs7769547, rs2268650, rs2894420, rs2268657, rs2268639, rs2268641, rs2300613, rs3799707, rs10305516, rs7766663, rs10305525, rs9296274, rs10305415). DNA was extracted from blood with a standard high-salt method. Genotyping was performed using customized GoldenGate Genotyping Assays (Illumina Inc, San Diego, Calif., USA).

The Statistical Package for the Social Sciences (SPSS), version 15.0, was used for association tests. Categorical variables were analyzed using Pearson's $\chi 2$. For continuous variables, we performed analysis of covariance (ANCOVA). Weight gain was calculated in % of baseline weight and genotype association with weight gain was analyzed using baseline weight and treatment duration as covariates since these variables had an influence on the observed weight gain). We carried out association tests in the total sample and in a more homogeneous subset of patients of European ancestry who were treated with clozapine or olanzapine only. Hardy-Weinberg-equilibrium and LD were calculated using Haploview version 4.2. Haplotype analysis for categorical variables was performed in haploview (>7% weight gain from baseline vs. <7% weight gain) and for quantitative variable (weight gain %) in UNPHASED version 3.1.4.

Gene-gene interaction was tested using the R-package mbmdr. To correct for multiple testing, we applied gene-wide Nyholt-correction.

Results

There were significant differences among the samples in terms of sex, age at study entry, ethnicity, baseline weight, study duration and medication (p<0.020). Patients treated with clozapine and olanzapine showed the highest weight gain. To account for the heterogeneity of the samples, we covaried for baseline weight and treatment duration in all following analyses and stratified the sample by ethnicity and medication. The subsample of European patients treated with clozapine or olanzapine (N=60) consisted of 20 female and 40 male patients with a mean age of 34.8+/−7.8 years and a mean weight change of 4.4+/−5.9% of baseline.

GCG and Weight Gain

All GCG polymorphisms were in Hardy-Weinberg-equilibrium (p>0.050). Due to low LD between the SNPs, no haplotype was constructed. In the overall sample, we observed significant association of rs13429709 with weight gain (p=0.040). This effect was even more pronounced in the refined sample of patients of European ancestry receiving clozapine or olanzapine (p=0.001) and remained significant after correction for multiple testing (pcorr=0.004). C-allele carriers showed the highest percent weight gain (CC (N=6): 9.77+/−3.98%; CT (N=26): 5.00+/=5.36%; TT (N=28): 2.73+/−6.22%).

Exploratory Combined Analysis of GCG and GLP1R

We conducted an exploratory analysis of gene-gene interaction between GCG and GLP1R. For this analysis we selected rs13429709 near GCG and rs2268639 in GLP1R which is near a histone binding site and had shown association with weight gain in the overall sample. We observed a highly significant interaction between rs13429709 and rs2268639 (p=0.0003). Weight gain was highly correlated with the number of present risk alleles with highest amount of gained weight in carriers of three or four risk alleles (defined as the C-allele in rs13429709 and T allele in rs2268639).

The results suggest that carriers of 3 or 4 risk alleles should not be treated with medications having an association with weight gain, such as clozapine and olanzapine.

2. Orexin Receptor 2 Genetic Markers

Patients were diagnosed with schizophrenia or schizoaffective disorder according to DSM-III-R or DSM-IV criteria (n=130). Written informed consent was obtained from all participants. Detailed demographic and clinical characteristics are provided in Table 5. Patients included in this study were 18 to 60 years old and were recruited from Case Western Reserve University, Cleveland, Ohio, USA (Sample HYM, n=74) and Hillside Hospital in Glen Oaks, N.Y., USA (Sample JAL, n=56). Patients were treated for 6 weeks or up to 14 weeks, respectively, and did not have any prior exposure to atypical antipsychotics. Exclusion criteria for these studies included pregnancy, organic brain disorder, severe head injuries, previous medical conditions which required treatment and were not stable (Hepatitis C, HIV, Thyroid disorder or diabetes mellitus), substance dependence, clinically relevant mental retardation and severe personality disorder.

Genomic DNA was extracted from blood samples using the high-salt method (Lahiri and Nurnberger 1991). Tag-SNPs were selected from the CEU population in HapMap (Haploview 4.2(Barrett et al. 2005)) using a region ~10 Kb upstream and 2 Kb downstream of the HCRTR1 and HCRTR2 genes (minor allele frequency>0.05, r2≥0.8). A total of 5 tagSNPs covering a 20 kb region including HCRTR1 (~9.6 kb) and 28 tagSNPs covering 120 kb including HCRTR2 (~108 kb) were included in this study. All genotyping was carried out using customised GoldenGate Genotyping Assays (Illumina, Inc. San Diego, Calif., USA). As a quality control ~5% of the total sample was re-genotyped and 100% concordance rate was observed in this study.

Statistical Analysis

Pearson's $\chi 2$ test for categorical variables and Student's t-test or analysis of variance for continuous variables was used for comparison (Statistical Package for the Social Sciences (SPSS), version 13.0). Analysis of covariance (ANCOVA) was used to test association between genotype and weight change (%) from baseline as the dependent variable, genotypes as fixed factor and, baseline weight and duration of treatment as covariates. Corrections for multiple tests were calculated using Single Nucleotide Polymorphism Spectral Decomposition (SNPSpD, (Nyholt 2004)). Power calculations were performed using Quanto 1.2.4 (Gauderman and Morrison 2006). Assuming a minor allele frequency of 0.25 and a sample size of n=130, we had more than 80% power to detect a mean difference of 3.6% between carriers and non-carriers of the risk genotype in an additive or dominant model.

Results

Among the clinical sites, no significant difference in the amount of weight gained was observed (Table 5). The baseline weight and the duration of treatment that were significantly different between the three sites were entered as covariates in all the association analysis. We did not observe association of any of the SNPs in the total sample (p>0.05). Considering that the overall sample consists of patients of diverse ancestry, and clozapine as well as olanzapine carry the highest risk of weight gain and have similar pharmacology, we stratified our sample and conducted a subgroup analysis on patients of European ancestry treated with clozapine or olanzapine. This subset consisted primarily of individuals who have had no or minimal exposure to atypical antipsychotic medications. We observed significant genotypic association of rs3134701, rs4142972, rs6922310, and rs2653350 (Table 6). Patients with risk genotypes, for example, AA genotype of rs6922310 or A-allele carriers for rs4142972 gained ~3.2 and ~4.8 kilograms more weight than the non-risk genotype. None of the SNPs in HCRTR1 was associated with AIWG (p>0.05).

TABLE 5

Clinical and Demographic Details.

| Characteristics | | Sample HYM n = 74 n (%) | Sample JAL n = 56 n (%) | Total n = 130 n (%) | p-value |
|---|---|---|---|---|---|
| Gender | Female | 27 (36.5) | 9 (16.1) | 36 (27.7) | 0.009 |
| | Male | 47 (63.5) | 47 (83.9) | 94 (72.3) | |
| Age | | 33.41 ± 8.5 | 41.3 ± 7.4 | 36.77 ± 8.9 | <0.001 |
| Initial bodyweight (kg) | | 75.05 ± 13.8 | 84.95 ± 17.4 | 79.22 ± 16.1 | <0.001 |
| Weight change (kg) | | 3.76 ± 4.4 | 4.43 ± 6.4 | 4.05 ± 5.4 | 0.486 |
| Weight change (%) | | 5.35 ± 6.3 | 5.73 ± 8.4 | 5.51 ± 7.3 | 0.768 |
| Weight gain | <7% | 47 (63.5) | 37 (66.1) | 84 (64.6) | 0.763 |
| | ≥7% | 27 (36.5) | 19 (33.9) | 46 (35.4) | |
| Baseline BPRS^ | | 51.23 ± 14.2 | 54.17 ± 7.7 | 52.66 ± 11.5 | 0.123* |
| Study duration (wk) | | 6.00 | 11.57 ± 3.9 | 8.40 ± 3.8 | <0.001* |
| Ethnicity | European-American | 52 (70.3) | 12 (21.4) | 64 (49.2) | <0.001 |
| | African-American | 22 (29.7) | 33 (58.9) | 55 (42.3) | |
| | Others | | 11 (19.7) | 11 (8.5) | <0.001 |
| Medications prescribed | Clozapine | 74 (100) | 12 (21.1) | 86 (65.6) | |
| | Haloperidol | — | 11 (19.3) | 11 (8.4) | |
| | Olanzapine | — | 22 (38.6) | 22 (16.8) | |
| | Risperidone | — | 12 (21.1) | 12 (9.2) | |

*Kruskal-Wallis test;
^BPRS: Brief Psychiatric Rating Scale. Baseline BPRS scores was available for a subset of the patients (n = 111). To achieve comparability with sample B, BPRS total scores were extracted from PANSS ratings for samples A and C.

TABLE 6

SNPs in orexin receptor 2 (HCRTR2) associated with antipsychotic induced weight gain at genotypic and/or allelic level.

| SNP | Location | Genotype | Weight change (%)* All patients (n = 130) | p-value | Weight change (%) European Ancestry (Cloz or Olz) (n = 60) | p-value | p-value (Dominant model) | HWE p-value |
|---|---|---|---|---|---|---|---|---|
| rs4467775 | 55036599 | GG | 5.47 ± 7.5 (88) | 0.470 | 3.15 ± 5.1 (37) | 0.149 | 0.073 | 0.636 |
| | | GC | 6.04 ± 6.9 (37) | | 6.91 ± 6.9 (21) | | 0.321# | |
| | | CC | 1.69 ± 5.0 (3) | | 1.55 ± 1.9 (2) | | | |
| rs3134701 | 55067318 | AA | 6.45 ± 6.1 (64) | 0.403 | 6.52 ± 5.8 (36) | 0.014 | 0.003 | 0.534 |
| | | AG | 4.28 ± 7.3 (51) | | 1.44 ± 4.9 (22) | | 0.045# | |
| | | GG | 5.38 ± 11.9 (13) | | −0.64 ± 6.4 (2) | | | |
| rs4142972 | 55076937 | GG | 5.38 ± 7.7 (93) | 0.869 | 2.81 ± 5.5 (39) | 0.020 | 0.005 | 0.275 |
| | | GA | 5.40 ± 6.5 (30) | | 7.46 ± 6.2 (17) | | 0.074# | |
| | | AA | 7.72 ± 3.7 (5) | | 7.19 ± 4.1 (4) | | | |
| rs6922310 | 55077184 | AA | 5.89 ± 6.6 (75) | 0.113 | 6.29 ± 5.8 (38) | 0.033 | 0.009 | 0.316 |
| | | AG | 3.98 ± 7.6 (45) | | 1.31 ± 4.9 (21) | | 0.134# | |
| | | GG | 10.17 ± 10.4 (8) | | −1.49 (1) | | | |
| rs12662510 | 55079891 | AA | 6.19 ± 7.2 (98) | 0.087 | 5.79 ± 6.1 (40) | 0.052 | — | 0.121 |
| | | AG | 3.14 ± 7.3 (30) | | 1.67 ± 4.7 (20) | | | |
| rs2653350 | 55144102 | AA | 7.64 ± 7.0 (38) | 0.128 | 7.33 ± 6.3 (19) | 0.013 | 0.011 | 0.657 |
| | | AG | 5.11 ± 7.5 (59) | | 3.83 ± 5.1 (28) | | 0.163# | |
| | | GG | 3.67 ± 6.8 (30) | | 1.43 ± 5.9 (13) | | | |

*Mean ± standard deviation (number of individuals);
HWE: Hardy Weinberg Equilibrium, calculated for the patients with European ancestry on RiskMed (clozapine and olanzapine).
P-values after accounting for the 14.84 independent tests.
Cloz or Olz = Olanzapine or Clozapine treated patients.

The correction for multiple comparisons was carried out using SNPSpD. The number of independent tests (MeffLi) for HCRTR2 was 14.84 (Nyholt 2004). The association of weight change and SNP rs3134701 remained significant in a dominant model at gene wide level (Pcorrected=0.045).

We further assessed the effect of the above SNPs in subjects of European ancestry who were treated with antipsychotics (haloperidol, quetiapine, aripiprazole, fluphenazine, amisulpride and ziprasidone) with low propensity to cause weight gain (n=34). No significant association of rs3134701, rs4142972 and rs6922310, and rs2653350 with antipsychotic induced weight gain was observed.

These results indicate that individuals carrying the risk alleles for weight gain should be treated with the lower risk antipsychotics to prevent unwanted weight gain.

3. Mitochondrial Genetic Markers in NDUFS1 and TSPO

Mitochondria are the main source of energy for neurons and play a role in many of the neuronal functions. Altered gene expression of mitochondrial genes has been described for schizophrenia and there is increasing evidence that antipsychotics such as clozapine and olanzapine may modulate mitochondrial function. In our study, we have worked with the hypothesis that nuclear-encoded mitochondrial genes, particularly those with altered gene expression or involved in oxidative phosphorylation, mitochondrial biogenesis, inflammation and apoptosis, are more likely to be associated with AIWG. To the best our knowledge, this is the first study to explore genetic variation in the mitochondrial genes in the context of AIWG. In total, 60 SNPs were genotyped in 77 individuals. The exact number of individuals used in each of the statistical analyses varied depending on the missing data rate of the covariates involved in that analysis. We have observed a significant association between rs6435326 and weight gain (%), (N=60, p=0.001). Two other SNPs, rs1053517 and rs1801318, within the same gene and moderately correlated with rs6435326 ($r2=0.5$, $D'=0.95$ and $r2=0.3$, $D'=1$, respectively), were nominally associated with weight gain (rs1053517, N=60, p=0.05; rs1801318 N=60, p=0.01). These SNPs are located within the NDUFS1 gene.

Patients 18 to 60 years old with schizophrenia or schizoaffective disorder were diagnosed according to DSM-III-R or DSM-IV criteria and recruited from two different investigators (total sample N=77): HYM-JAL (Cleveland/North Carolina, USA, N=40); DJM-2 (Toronto, Canada, N=37). For this study, only individuals with European ancestry (self-report) were genotyped. A complete description of the study was provided to the participants and written informed consent was obtained in line with each institution's ethics review board guidelines. For HYM and JAL samples patients did not have any prior exposure to SGAs and were treated for 6 weeks, or up to 14 weeks. For sample DJM-2, patients were prescribed antipsychotic medication and followed up for a minimum of 6 weeks. Demographic and clinical characteristics of the sample stratified by the two samples are provided in Table 7.

TABLE 7

Demographic and clinical characteristics of samples.

|  | HYM/JAL | DJM-2 | Total Sample | P value |
|---|---|---|---|---|
| Number of Individuals | 40 | 37 | 77 |  |
| Weight gain (%) | 5.27 ± 5.89 | 3.4 ± 8.98 | 4.49 ± 7.36 | 0.039[a] |
| Baseline weight (kg) | 75.02 ± 13.58 | 86.24 ± 19.26 | 80.24 ± 17.29 | 0.010[a] |
| Age (years) | 35.05 ± 7.59 | 38.43 ± 11.82 | 36.68 ± 9.93 | 0.137[b] |
| Study duration (weeks) | 6.27 ± 1.96 | 5.59 ± 1.24 | 5.99 ± 1.71 | 0.082[a] |
| Sex: |  |  |  | 0.361[c] |
| Male | 26 (65%) | 23 (70%) | 49 (67%) |  |
| Female | 14 (35%) | 10 (30%) | 24 (33%) |  |
| Medication: |  |  |  | 0.057[c] |
| Clozapine/Olanzapine | 40 (100.0%) | 23 (88.5%) | 63 (95.4%) |  |
| Others |  | 3 (11.5%) | 3 (4.6%) |  |

Only Europeans were included in the study.
[a]Kruskal-Wallis Test,
[b]ANOVA,
[c]Chi-square test.
*Age at recruitment.

Our replication study of rs6435326, rs1053517 and rs1801318 in NDUFS1 using samples from the Clinical Antipsychotic Trials of Intervention Effectiveness (CATIE) showed that rs1801318 was significantly associated with AIWG (N=200, Pcorrected=0.04, Table 8). The association between rs6435326 and AIWG was not statistically significant in the CATIE replication sample (P=0.18, Table 8). However, direction of effect is consistent with the discovery sample. Notably, the CATIE sample consists of chronic subjects and they may have already experienced treatment with second generation medications in the past. Finally, the gene-based replication study (joint analysis of all three SNPs) replicated the finding that NDUFS1 is associated with AIWG (P=0.04).

TABLE 8

Replication of the top three SNPs in NDUFS1

| Marker | Gene | MAF | LD[a] | Discovery Sample β | P* | Replication Sample β | P* | INFO[b] |
|---|---|---|---|---|---|---|---|---|
| rs6435326 | NDUFS1 | 0.47 | — | −2.818 | 0.001 | −1.34 | 0.18 | NA |
| rs1053517 | NDUFS1 | 0.43 | 0.8 | −1.843 | 0.05 | −1.98 | 0.04 | 0.94 |
| rs1801318 | NDUFS1 | 0.30 | 0.4 | −2.734 | 0.01 | −2.29 | 0.02 | 0.94 |

[a]measured by $r^2$ between the SNP and rs6435326.
[b]genotype of rs6435326 was obtained using the TaqMan SNP Genotyping Assays (Applied Biosystems Inc, Foster City, CA), and INFO was imputation accuracy measure provided by IMPUTE v2.2 (Howie et al, 2012).
*p-values are not corrected for multiple testing. Nyholt $p_{corrected}$ = 53 (independent SNPs) * p-value (Discovery sample), Nyholt $p_{corrected}$ = 2 * p-value (Replication sample), bolded p-values remained significant after multiple testing correction.

These results indicate that SNPs rs6435326, rs1801318 and rs1053517 are strong candidates for inclusion in panels of genetic markers for antipsychotic response and side-effects, particularly risk of weight gain.

TSPO

Study subjects. Our sample comprised 66 European ancestry subjects aged 18-60 years with schizophrenia or schizoaffective disorder according to Diagnostic and Statistical Manual of Mental Disorders, Third Edition, Revised, or Fourth Edition (DSM-IIIR or DSM-IV) criteria. Subjects were recruited from two study centres, and clinical and demographic characteristics for each centre are described in Table 9. Written informed consent was obtained for all participants, in accordance with each institution's Research Ethics Board approval.

Sample HYM, Case Western Reserve University in Cleveland, Ohio, USA (HY Meltzer and JA Lieberman, n=54). Patients with a history of treatment refractory schizophrenia or schizoaffective disorder, or intolerance to typical antipsychotics, were treated with clozapine for 6 weeks and assessed for response and weight gain. These patients had never received a second generation antipsychotic prior to enrollment in the study, and underwent a 7-14 day washout period where they received no antipsychotic medication prior to receiving clozapine. Serum levels of clozapine were also monitored for compliance (for further details, see (Tiwari et al., 2010)).

Sample JAL, Hillside Hospital in Glen Oaks, N.Y., USA (J A Lieberman, n=12). Patients with a suboptimal response to previous treatment with typical antipsychotics were treated with clozapine, olanzapine, risperidone, or haloperidol and were assessed for response and weight gain in a 14-week prospective, double-blind randomized controlled trial (for further details, see (Volavka et al., 2002).

Genetic Typing

Venous blood (10-20 mL) was obtained from patients in two 10 $cm^3$ EDTA tubes, and genomic DNA was extracted from blood lymphocytes using a high salt method (Lahiri and Nurnberger, 1991).

Given accumulating evidence that common SNPs involved in schizophrenia and other psychiatric disorders frequently act by causing changes in gene expression rather than alterations in protein structure (Richards et al., 2012), SNPs were selected based on evidence of regulatory function. All SNPs with scores of if or greater in RegulomeDB (Dunham et al., 2012) within 10 kb upstream or downstream of TSPO were selected for genotyping (rs138926, rs80411, rs6971, rs113515, rs138911, rs5759197, rs739092). Marker rs6973, located in the 3' UTR of TSPO, was also selected based on miRNA binding and regulatory potential from SNPinfo (Xu and Taylor, 2009). Selected SNPs captured 77% of common alleles across the TSPO gene region.

Genotyping was done using Assays-on-Demand for all SNPS with the TaqMan allele specific assay method, using the Viia7 Sequence Detection System (Applied Biosystems, Foster City, Calif., USA). PCR was performed in a final reaction volume of 104, consisting of 20 ng of genomic DNA, 2× TaqMan Universal Master Mix, and 40×SNP Genotyping Assay Mix (Applied Biosystems, Foster City, Calif., USA), and amplification under the following conditions: 95° C. for 10 min, followed by 50 cycles of 92° C. for 15 s and 60° C. for 1 min Genotypes were determined with the Applied Biosystems allelic discrimination software, and confirmed independently by two experienced researchers. Genotype call rates were >95% for all eight markers. Replication was performed for a random sample of 10% of study subjects for quality control, with 100% concordant genotypes observed.

Statistical Analyses

All analyses were done using R version 2.15.1 statistical software (R Core Team, 2012), with the rms package. Categorical variables were compared across study centres using Pearson chi-square test and continuous variables were compared using ANOVA, unless the assumptions of these tests were violated in which case Fisher's exact test and the Kruskal-Wallis test were used. Linear regression was used to test for differences in weight gain (% change from baseline weight) between genotypic groups using additive genotypic model with adjustment for relevant covariates. Two a priori analyses were conducted, the first in the total sample including subjects treated with all antipsychotics, and the second in the subset of subjects treated with clozapine or olanzapine (due to the greater propensity of these medications to cause weight gain). The Nyholt method was used to correct for multiple testing (Nyholt, 2004). Linkage disequilibrium structure and Hardy-Weinberg equilibrium were determined using Haploview version 4.2 (Barrett et al., 2005).

Results

All eight SNPs were in Hardy-Weinberg equilibrium in the total sample (p>0.05). There were 5 independent tests in our total sample, resulting in an experiment-wide threshold for significance of 0.01 (Nyholt, 2004). Several clinical variables were different across the four study centres (Table 9). However, the outcome measure % weight change was similar across study sites (p=0.83).

In the sample analyzed here, subjects from Samples HYM and JAL treated with clozapine or olanzapine, there was no significant correlation between change in weight (%) and sex (p=0.92), age (p=0.81), duration of treatment (p=0.86), or antipsychotic prescribed (p=0.15). There was significant correlation between change in weight (%) and baseline weight (p=0.02). Therefore, all linear regression models of change in weight (%) were adjusted for baseline weight.

No significant association was observed between any of the TSPO polymorphisms and weight change (%) in the total sample of subjects treated with one of a variety of antipsychotics (pcorrected>0.05). We observed greatest weight gain among subjects treated with clozapine (3.99%±5.8) or olanzapine (10.25%±12.9) compared to haloperidol (−4.17%±15.2), or risperidone (0.77) in our total sample. Given the greater propensity of clozapine and olanzapine to cause weight gain in our sample, which is consistent with previous literature (review by Lett et al., 2012), we performed a secondary analysis on the subset of subjects in Samples HYM and JAL treated with clozapine or olanzapine (n=62, Table 10 below). In this secondary analysis, rs6971 showed significant association with % weight change using an additive genotypic model ($p_{corrected}$=0.04). Marker rs6971 is a non-synonymous SNP, with the G allele coding for alanine (Ala) at amino acid position 147 of the TSPO protein, and the A allele coding for threonine (Thr). In our sample, 'Thr' allele homozygotes gained more weight (9.77%±6.4) than heterozygotes (4.48%±8.2) or 'Ala' homozygotes (2.3%±4.6).

Notably, rs6971 is a functional polymorphism and shows robust association with TSPO binding affinity, both in vitro (Owen et al., 2012) and in vivo (Mizrahi et al., 2012, Kreisl et al., 2013). The 'Thr' allele is associated with much lower TSPO binding affinity than the 'Ala' allele, and individuals homozygous for 'Thr' have little to no binding of TSPO-specific PET radioligands. While previous studies have found no association between TSPO polymorphisms and schizophrenia diagnosis (Kurumaji et al., 2000, Fallin et al., 2005), this is the first study to investigate TSPO polymorphisms in association with AIWG.

TABLE 9

Demographic and clinical characteristics of study sample.

| | Sample HYM (n = 54)[a] Cleveland | Sample JAL (n = 12)[a] New York/ North Carolina | p-value |
|---|---|---|---|
| Male (%) | 33 (61) | 12 (100) | 0.007[b] |
| Age at recruitment ± SD (years) | 34.95 ± 7.7 | 41.25 ± 5.1 | 0.02[c] |
| Study duration ± SD (weeks) | 6.00 ± 0.0 Treatment | 10.83 ± 4.1 | <0.001[c] |
| Clozapine (%) | 54 (100) | 6 (50) | <0.001[b] |
| Haloperidol (%) | | 3 (25) | |
| Olanzapine (%) | | 2 (17) | |
| Risperidone (%) | | 1 (8) | |
| Baseline weight ± SD (kg) | 79.37 ± 14.1 | 83.86 ± 17.6 | 0.04[d] |
| Weight change ± SD (%) | 3.84 ± 5.8 | 3.38 ± 9.9 | 0.83[d] |
| Baseline BPRS ± SD | 51.54 ± 15.4 | 52.58 ± 8.8 | 0.77[c] |
| BPRS change ± SD | −10.88 ± 12.4 | −3.00 ± 11.8 | 0.11[c] |

[a]The total sample comprised subjects from two different clinical studies;
[b]Fisher's exact test;
[c]Kruskal Wallis test;
[d]ANOVA test

TABLE 10

Association between SNPs in TSPO region and weight gain induced by clozapine or olanzapine in HYM and JAL samples (N = 62)

| SNP chr: bp[a] | Genotype | % weight change ± SD (N) | $p_{uncor}$ | Allele | % weight change ± SD (allele count, freq) | $p_{uncor}$ |
|---|---|---|---|---|---|---|
| rs739092 chr22: 43544823 | CC | 4.95 ± 6.1 (33) | 0.46 | C | 4.83 ± 6.1 (91, 0.71) | 0.38 |
| | CT | 4.52 ± 6.3 (25) | | T | 3.89 ± 6.1 (37, 0.29) | |
| | TT | 2.58 ± 5.9 (6) | | | | |
| rs5759197 chr22: 43550149 | TT | 5.18 ± 6.2 (31) | 0.58 | T | 4.79 ± 6.1 (88, 0.69) | 0.49 |
| | TC | 3.85 ± 5.8 (26) | | C | 4.04 ± 6.2 (40, 0.31) | |
| | CC | 4.40 ± 7.3 (7) | | | | |
| rs138911 chr22: 43553417 | GG | 3.27 ± 5.3 (36) | 0.15 | G | 3.58 ± 5.5 (96, 0.74) | 0.05 |
| | GT | 4.51 ± 6.3 (24) | | T | 6.71 ± 7.3 (34, 0.26) | |
| | TT | 12.00 ± 7.6 (5) | | | | |
| rs113515 chr22: 43556922 | CC | 5.59 ± 7.7 (21) | 0.32 | C | 5.34 ± 6.8 (73, 0.56) | 0.20 |
| | CG | 4.99 ± 5.7 (31) | | G | 3.19 ± 5.0 (57, 0.44) | |
| | GG | 1.04 ± 3.0 (13) | | | | |
| rs6971[b] chr22: 43558926 | Ala/Ala | 2.29 ± 6.9 (35) | 0.008 | G | 3.13 ± 5.3 (95, 0.72) | 0.002 |
| | Ala/Thr | 5.46 ± 6.6 (25) | | A | 7.38 ± 7.1 (37, 0.28) | |
| | Thr/Thr | 11.37 ± 4.6 (6) | | | | |
| rs6973 chr22: 43559137 | GG | 5.67 ± 6.4 (35) | 0.19 | G | 4.79 ± 6.4 (96, 0.74) | 0.16 |
| | GT | 2.42 ± 5.9 (26) | | T | 3.29 ± 5.5 (34, 0.26) | |
| | TT | 6.14 ± 2.7 (4) | | | | |
| rs80411 chr22: 43561675 | GG | 2.97 ± 4.2 (32) | 0.05 | G | 3.26 ± 5.1 (88, 0.68) | 0.01 |
| | GT | 4.02 ± 7.2 (24) | | T | 6.78 ± 7.4 (42, 0.32) | |
| | TT | 10.47 ± 6.2 (9) | | | | |
| rs138926 chr22: 43562306 | GG | 2.97 ± 4.2 (32) | 0.05 | G | 3.26 ± 5.1 (88, 0.68) | 0.01 |
| | GA | 4.02 ± 7.2 (24) | | A | 6.78 ± 7.4 (42, 0.32) | |
| | AA | 10.47 ± 6.2 (9) | | | | |

[a]Locations based on Genome Reference Consortium Build 37;
[b]rs6971 is a non-synonymous SNP, the G allele results in the addition of alanine (Ala) at amino acid position 147 of the TSPO protein, while the A allele results in the addition of threonine (Thr);
p-values are not corrected for multiple testing Nyholt $p_{corrected}$ = 5 * p-value; bolded p-values remained significant after multiple testing correction.

pital in Glen Oaks, N.Y., USA (Sample JAL, n=8). Patients from sample HYM and JAL, were treated for 6 weeks or up to 14 weeks, respectively, and did not have any prior exposure to atypical antipsychotics. Exclusion criteria for these studies included pregnancy, organic brain disorder, severe head injuries, previous medical conditions which required treatment and were not stable (Hepatitis C, HIV, Thyroid disorder or diabetes mellitus), substance dependence, clinically relevant mental retardation and severe personality disorder.

Genomic DNA was extracted from blood samples using the high-salt method (Lahiri and Nurnberger 1991). Single nucleotide polymorphisms (SNPs) were genotyped using TaqMan® SNP Genotyping Assays (rs806378, rs16147 and rs489693; Applied Biosystems Inc, Foster City, Calif.) or using customized GoldenGate Genotyping Assays (rs13429709, rs3134701 and rs4142972, Illumina, Inc. San Diego, Calif., USA).

Statistical analysis. Differences between the demographic variables among the clinical sites were tested using $\chi 2$ or T-test. Analysis of variance or Analysis of covariance (ANCOVA) was used to test association between genotype and weight change (%) from baseline as the dependent variable, 4. Panels of Genetic Markers for the Treatment and Prevention of Antipsychotic Medication-Induced Weight Gain Subjects. Patients were diagnosed with schizophrenia or schizoaffective disorder according to DSM-III-R or DSM-IV criteria (n=60). Written informed consent was obtained from all participants. Detailed demographic and clinical characteristics are provided in Table 11 and have been published previously (Tiwari et al. 2010; Tiwari et al. 2013). Patients included in this study were 18 to 60 years old and were recruited from Case Western Reserve University, Cleveland, Ohio, USA (Sample HYM, n=52); Hillside Hospital in Glen Oaks, N.Y., USA (Sample JAL, n=8).

genotypes as fixed factor and, baseline weight and duration of treatment as covariates (Statistical Package for the Social Sciences (SPSS), version 13.0).

Results

The results above demonstrate that SNPs in or near GCG (rs13429709), HCRTR2 (rs3134701 and rs4142972), TSPO (rs6971) and NDUFS1 (rs6435326) are significantly associated with AIWG. In addition, we have previously reported that CNR1 (rs806378), NPY (rs16147), and MC4R (rs489693) are significantly associated with AIWG (Tiwari et al., 2010; 2013; Malhotra et al., 2012).

Here, we determined the mode of inheritance for each of these SNPs using a post hoc pair-wise comparison of mean AIWG among the genotypic groups. The risk alleles at rs806378-A (vs. C-allele), rs16147-C (vs. T-allele), rs13429709-C (vs. T-allele), rs4142972-A (vs. G-allele) and rs6971-A (vs G-allele) appeared to have a dominant effect whereas rs489693-A (vs. C-allele), rs3134701-A (vs. G-allele) and rs6435326-A (vs-T allele) had a recessive effect on AIWG. Based on the above post hoc comparisons, genotypes were re-coded as '0'=no risk or as '1'=at risk for AIWG. The total genetic risk score for each individual was then determined by adding genotypes at all the four loci leading to a score ranging from 0 (no-risk) to 8 (highest risk). This score was then entered as a factor in ANCOVA to determine the cumulative effect of these variants on AIWG. The above comparison was corrected for the effect of baseline weight and duration of treatment by using them as covariates. We observed a statistically significant difference in the amount of weight gained in the different risk score categories (Tables 13-16 and 18). In the overall model including eight SNPs, individuals who carried zero up to three risk variant gained the least amount of weight (0.81±3.7) compared to individuals with four or more risk alleles. Overall, this risk score model incorporating baseline weight and duration of treatment along with the eight SNPs has the highest amount of variance explained (68.1%) compared to other risk models with less number of SNPs (n=37, Tables 13-16 and 18). This risk model was also evaluated in subjects of European ancestry who were treated with antipsychotics (haloperidol, quetiapine, aripiprazole, fluphenazine, amisulpride and ziprasidone) with low propensity to cause weight gain (n=30). The overall model did not predict weight gain with these antipsychotics (Table 17). Thus, the risk model predicts weight gain only when subjects are treated with high weight gain risk medications (e.g. clozapine and olanzapine). These individuals should be treated with alternative antipsychotics having a low propensity for inducing weight gain in order to prevent unwanted weight gain.

TABLE 11

Demographic characteristics of the sample used for the risk model

| Characteristics | Sample HYM | Sample JAL | Total | p-value |
|---|---|---|---|---|
| Males/females | 32/20 | 8/0 | 40/20 | 0.043 |
| Age | 33.63 ± 7.5 | 42.15 ± 4.8 | 34.77 ± 7.8 | 0.003 |
| Duration of treatment | 6.00 | 10.63 ± 3.7 | 6.62 ± 2.0 | <0.001* |
| Baseline weight | 74.55 ± 14.1 | 82.90 ± 16.9 | 75.66 ± 14.59 | 0.133 |
| Weight change (kg) | 2.83 ± 4.0 | 4.49 ± 4.3 | 3.05 ± 4.1 | 0.289 |
| Weight change (%) | 4.09 ± 5.8 | 6.54 ± 7.1 | 4.42 ± 5.9 | 0.283 |
| Clozapine/olanzapine | 52/0 | 6/2 | 58/2 | 0.016 |

*Kruskal-Wallis test

TABLE 12

Association of single SNPs with antipsychotic induced weight gain.

| Gene | SNP | Genotype | Weight change (%) | p-value | Weight change (%) Dominant model | p-value | Weight change (%), Recessive model | p-value | Variance[#] |
|---|---|---|---|---|---|---|---|---|---|
| CNR1 | rs806378 | CC | 2.10 ± 5.1 (29) | 0.021 | 2.10 ± 5.1 (29) | 0.006 | — | — | 18.4 |
|  |  | CT | 6.99 ± 5.9 (28) |  | 6.86 ± 2.9 (30) |  |  |  |  |
|  |  | TT | 4.92 ± 6.9 (2) |  |  |  |  |  |  |
| NPY | rs16147 | AA | 2.02 ± 5.6 (19) | 0.014 | 2.02 ± 5.6 (19) | 0.004 | 4.30 ± 5.7 (48) | 0.257 | 20.3 |
|  |  | GA | 5.80 ± 5.2 (29) |  | 5.85 ± 5.8 (39) |  |  |  |  |
|  |  | GG | 5.99 ± 7.6 (10) |  |  |  | 5.99 ± 7.6 (10) |  |  |
| GCG | rs13429709 | TT | 2.73 ± 6.2 (28) | 0.001 | 2.73 ± 6.2 (28) | 0.001 | 3.82 ± 5.9 (54) | 0.011 | 23.5 |
|  |  | TC | 5.00 ± 5.4 (26) |  | 5.90 ± 5.4 (32) |  |  |  |  |
|  |  | CC | 9.77 ± 4.0 (6) |  |  |  | 9.77 ± 4.0 (6) |  |  |
| MC4R | rs489693 | CC | 3.87 ± 5.6 (35) | 0.206 | 3.87 ± 5.6 (35) | 0.207 | 4.07 ± 5.7 (50) | 0.094 | 11.8 |
|  |  | AC | 4.53 ± 6.2 (15) |  | 5.74 ± 6.5 (20) |  |  |  |  |
|  |  | AA | 9.37 ± 7.0 (5) |  |  |  | 9.37 ± 7.0 (5) |  |  |
| HCRTR2 | rs3134701* | AA | 6.52 ± 5.8 (36) | 0.014 | — | — | 6.52 ± 5.8 (36) | 0.003 | 20.8 |
|  |  | AG | 1.44 ± 4.9 (22) |  |  |  | 1.27 ± 4.7 (24) |  |  |
|  |  | GG | −0.64 ± 6.4 (2) |  |  |  |  |  |  |
|  | rs4142972 | GG | 2.81 ± 5.5 (39) | 0.020 | 2.81 ± 5.5 (39) | 0.005 | — | — | 19.9 |
|  |  | GA | 7.46 ± 6.2 (17) |  | 7.41 ± 5.7 (21) |  |  |  |  |
|  |  | AA | 7.19 ± 4.1 (4) |  |  |  |  |  |  |
| TSPO | rs6971 | Ala/Ala (GG) | 2.69 ± 4.6 (30) | 0.070 | 2.69 ± 4.6 (30) | 0.034 | 3.97 ± 5.8 (54) | 0.148 | 15.2 |
|  |  | Ala/Thr (GA) | 5.56 ± 6.7 (24) |  | 6.29 ± 6.0 (29) |  |  |  |  |
|  |  | Thr/Thr (AA) | 9.77 ± 6.4 (5) |  |  |  | 9.77 ± 6.4 (5) |  |  |
| NDUFS1 | rs6435326* | AA | 8.43 ± 5.9 (15) | 0.030 | 6.33 ± 5.6 (28) | 0.123 | 8.43 ± 5.9 (15) | 0.008 | 26.1 |
|  |  | AT | 3.91 ± 4.4 (13) |  |  |  | 3.33 ± 5.2 (23) |  |  |
|  |  | TT | 2.58 ± 6.2 (10) |  | 2.58 ± 6.2 (10) |  |  |  |  |

*The major allele has been considered to be the risk allele for AIWG. All other models are with respect to the minor allele;

[#]Variance explained is for the model with highest significance.

TABLE 13

Distribution of weight change (%) across risk score categories using two SNP combinations.

| Genes | SNPs | No of risk genotypes | No of individuals | Weight change (%) | P-value | Variance explained |
|---|---|---|---|---|---|---|
| GCG, HCRTR2 | rs13429709, rs4142972 | 0 | 21 | 1.51 +/− 6.1 | 0.00032 | 29.8 |
| | | 1 | 25 | 4.89 +/− 4.8 | | |
| | | 2 | 14 | 7.92 +/− 6.0 | | |
| GCG, HCRTR2 | rs13429709, rs3134701 | 0 | 13 | (−).51 +/− 4.1 | 0.00022 | 30.8 |
| | | 1 | 26 | 4.62 +/− 5.8 | | |
| | | 2 | 21 | 7.21 +/− 5.4 | | |
| GCG, TSPO | rs13429709, rs6971 | 0 | 15 | 1.64 +/− 5.2 | 0.0015 | 26.3 |
| | | 1 | 27 | 3.92 +/− 5.6 | | |
| | | 2 | 17 | 7.80 +/− 5.9 | | |
| GCG, NDUFS1 | rs13429709, rs6435326 | 0 | 10 | 2.42 +/− 5.5 | 0.002 | 35.1 |
| | | 1 | 17 | 4.71 +/− 5.6 | | |
| | | 2 | 11 | 8.98 +/− 5.5 | | |
| HCRTR2 | rs4142972, rs3134701 | 0 | 19 | (−).08 +/− 3.7 | 0.0005 | 28.6 |
| | | 1 | 25 | 5.72 +/− 5.4 | | |
| | | 2 | 16 | 7.72 +/− 6.1 | | |
| HCRTR2, TSPO | rs4142972, rs6971 | 0 | 22 | 2.01 +/− 4.7 | 0.003 | 24 |
| | | 1 | 24 | 4.15 +/− 5.8 | | |
| | | 2 | 13 | 9.17 +/− 5.9 | | |
| HCRTR2, NDUFS1 | rs4142972, rs6435326 | 0 | 12 | .25 +/− 3.6 | 0.00012 | 45.6 |
| | | 1 | 18 | 6.60 +/− 4.7 | | |
| | | 2 | 8 | 10.16 +/− 6.3 | | |
| HCRTR2, TSPO | rs3134701, rs6971 | 0 | 14 | .45 +/− 3.8 | 0.0015 | 26.2 |
| | | 1 | 26 | 3.80 +/− 5.1 | | |
| | | 2 | 19 | 8.32 +/− 6.4 | | |
| HCRTR2, NDUFS1 | rs3134701, rs6435326 | 0 | 12 | 1.77 +/− 5.4 | 0.00059 | 40.1 |
| | | 1 | 14 | 4.34 +/− 4.5 | | |
| | | 2 | 12 | 10.10 +/− 5.2 | | |
| TSPO, NDUFS1 | rs6971, rs6435326 | 0 | 9 | 2.77 +/− 4.7 | 0.0024 | 34.8 |
| | | 1 | 22 | 4.02 +/− 4.9 | | |
| | | 2 | 7 | 12.81 +/− 4.7 | | |

TABLE 14

Distribution of weight change (%) across risk score categories using three SNP combinations.

| Genes | SNPs | No of risk genotypes | No of individuals | Weight change (%) | P-value | Variance explained |
|---|---|---|---|---|---|---|
| GCG, HCRTR2 | rs13429709, rs4142972, rs3134701 | 0 | 11 | (−)1.46 +/− 3.7 | $7.17 \times 10^{-5}$ | 35.8 |
| | | 1 | 20 | 3.60 +/− 5.1 | | |
| | | 2 | 18 | 6.71 +/− 5.2 | | |
| | | 3 | 11 | 8.04 +/− 6.2 | | |
| GCG, HCRTR2, TSPO | rs13429709, rs4142972, rs6971 | 0 | 12 | .68 +/− 4.7 | 0.00044 | 31.8 |
| | | 1 | 21 | 3.53 +/− 6.1 | | |
| | | 2 | 17 | 5.27 +/− 4.4 | | |
| | | 3 | 9 | 10.11 +/− 6.2 | | |
| GCG, HCRTR2, NDUFS1 | rs13429709, rs4142972, rs6435326 | 0 | 6 | (−)1.70 +/− 4.9 | $6.9 \times 10^{-5}$ | 50.6 |
| | | 1 | 12 | 3.08 +/− 4.5 | | |
| | | 2 | 14 | 7.57 +/− 4.8 | | |
| | | 3 | 6 | 10.21 +/− 6.7 | | |
| GCG, HCRTR2, TSPO | rs13429709, rs3134701, rs6971 | 0 | 7 | (−).53 +/− 4.6 | 0.0001 | 35.6 |
| | | 1 | 21 | 1.69 +/− 4.4 | | |
| | | 2 | 18 | 6.99 +/− 5.4 | | |
| | | 3 | 13 | 8.11 +/− 6.2 | | |
| GCG, HCRTR2, NDUFS1 | rs13429709, rs3134701, rs6435326 | 0 | 5 | (−).81 +/− 4.4 | 0.00028 | 45.9 |
| | | 1 | 14 | 4.00 +/− 5.0 | | |
| | | 2 | 9 | 6.12 +/− 5.5 | | |
| | | 3 | 10 | 9.60 +/− 5.4 | | |
| GCG, TSPO, NDUFS1 | rs13429709, rs6971, rs6435326 | 0 | 3 | 6.70 +/− 6.2 | $3.17 \times 10^{-5}$ | 53.0 |
| | | 1 | 15 | .77 +/− 3.5 | | |
| | | 2 | 15 | 7.13 +/− 4.6 | | |
| | | 3 | 5 | 12.90 +/− 5.4 | | |
| HCRTR2, TSPO | rs4142972, rs3134701, rs6971 | 0 | 13 | .12 +/− 3.8 | 0.00062 | 30.8 |
| | | 1 | 16 | 2.78 +/− 4.9 | | |
| | | 2 | 21 | 5.95 +/− 5.6 | | |
| | | 3 | 9 | 10.21 +/− 6.1 | | |
| HCRTR2, NDUFS1 | rs4142972, rs3134701, rs6435326 | 0 | 9 | (−).52 +/− 3.1 | $9.88 \times 10^{-5}$ | 49.5 |
| | | 1 | 8 | 4.28 +/− 5.4 | | |
| | | 2 | 14 | 6.93 +/− 4.1 | | |
| | | 3 | 7 | 10.93 +/− 6.4 | | |

TABLE 14-continued

Distribution of weight change (%) across risk score categories using three SNP combinations.

| Genes | SNPs | No of risk genotypes | No of individuals | Weight change (%) | P-value | Variance explained |
|---|---|---|---|---|---|---|
| HRCRTR2, TSPO, NDUFS1 | rs4142972, rs6971, rs6435326 | 0 | 6 | 1.19 +/− 3.2 | 0.0001 | 49.3 |
| | | 1 | 13 | 2.40 +/− 5.4 | | |
| | | 2 | 15 | 6.85 +/− 3.8 | | |
| | | 3 | 4 | 15.50 +/− 3.5 | | |
| HCRTR2, TSPO, NDUFS1 | rs3134701, rs6971, rs6435326 | 0 | 5 | (−).12 +/− .26 | 0.0015 | 39.6 |
| | | 1 | 14 | 3.76 +/− 5.8 | | |
| | | 2 | 12 | 5.12 +/− 3.9 | | |
| | | 3 | 7 | 12.81 +/− 4.7 | | |

TABLE 15

Distribution of weight change (%) across risk score categories using four or five SNP combinations

| Genes | SNPs | No of risk genotypes | No of individuals | Weight change (%) | P-value | Variance explained |
|---|---|---|---|---|---|---|
| GCG, HCRTR2, TSPO | rs13429709, rs4142972, rs3134701, rs6971 | 0 | 6 | (−)1.41 +/− 4.3 | $3.14 \times 10^{-5}$ | 40.4 |
| | | 1 | 19 | 1.25 +/− 3.8 | | |
| | | 2 | 10 | 7.64 +/− 6.0 | | |
| | | 3 | 18 | 5.71 +/− 4.9 | | |
| | | 4 | 6 | 11.41 +/− 6.1 | | |
| GCG, HCRTR2, NDUFS1 | rs13429709, rs4142972, rs3134701, rs6435326 | 0 | 4 | (−)2.19 +/− 3.6 | $2.37 \times 10^{-5}$ | 56.6 |
| | | 1 | 9 | 1.59 +/− 3.3 | | |
| | | 2 | 9 | 6.56 +/− 4.8 | | |
| | | 3 | 10 | 7.73 +/− 4.9 | | |
| | | 4 | 6 | 10.21 +/− 6.7 | | |
| GCG, HCRTR2, TSPO, NDUFS1 | rs13429709, rs4142972, rs6971, rs6435326 | 0 | 2 | 3.87 +/− 5.5 | $1.04 \times 10^{-5}$ | 58.9 |
| | | 1 | 10 | .08 +/− 4.9 | | |
| | | 2 | 12 | 4.77 +/− 3.3 | | |
| | | 3 | 11 | 8.24 +/− 4.7 | | |
| | | 4 | 3 | 15.57 +/− 4.3 | | |
| GCG, HCRTR2, TSPO, NDUFS1 | rs13429709, rs3134701, rs6971, rs6435326 | 0 | 1 | 0 | 0.00063 | 45.7 |
| | | 1 | 12 | 1.50 +/− 5.2 | | |
| | | 2 | 9 | 4.68 +/− 4.4 | | |
| | | 3 | 11 | 7.13 +/− 4.7 | | |
| | | 4 | 5 | 12.90 +/− 5.4 | | |
| HCRTR2, TSPO, NDUFS1 | rs3134701, rs4142972, rs6971, rs6435326 | 0 | 5 | (−).12 +/− .3 | $1.61 \times 10^{-5}$ | 57.7 |
| | | 1 | 7 | .59 +/− 5.0 | | |
| | | 2 | 11 | 5.95 +/− 5.0 | | |
| | | 3 | 11 | 6.56 +/− 3.7 | | |
| | | 4 | 4 | 15.50 +/− 3.5 | | |
| GCG, HCRTR2, TSPO, NDUFS1 | rs13429709, rs3134701, rs4142972, rs6971, rs6435326 | 0 | 1 | 0 | $2.68 \times 10^{-5}$ | 58.6 |
| | | 1 | 9 | (−).42 +/− 3.9 | | |
| | | 2 | 6 | 4.86 +/− 4.1 | | |
| | | 3 | 10 | 6.16 +/− 4.6 | | |
| | | 4 | 9 | 7.72 +/− 4.7 | | |
| | | 5 | 3 | 15.57 +/− 4.2 | | |

TABLE 16

Distribution of weight change (%) across risk score categories using six, seven or eight SNP combinations

| Genes | SNPs | No of risk genotypes | No of individuals | Weight change (%) | P-value | Variance explained |
|---|---|---|---|---|---|---|
| GCG, HCRTR2, TSPO, NDUFS1, CNR1 | rs13429709, rs3134701, rs4142972, rs6971, rs6435326, rs806378 | 0 | 0 | — | $2.84 \times 10^{-6}$ | 64.7 |
| | | 1 | 8 | (−)1.44 +/− 2.6 | | |
| | | 2 | 3 | 3.50 +/− 3.9 | | |
| | | 3 | 10 | 4.51 +/− 4.3 | | |
| | | 4 | 9 | 7.93 +/− 3.8 | | |
| | | 5 | 6 | 8.66 +/− 5.0 | | |
| | | 6 | 2 | 17.85 +/− 2.2 | | |
| GCG, HCRTR2, TSPO, NDUFS1, | rs13429709, rs3134701, rs4142972, rs6971, | 0 | 1 | 0 | 0.00029 | 53.1 |
| | | 1 | 3 | −2.53 +/− 4.4 | | |
| | | 2 | 7 | 2.31 +/− 5.5 | | |
| | | 3 | 5 | 3.36 +/− 2.1 | | |

TABLE 16-continued

Distribution of weight change (%) across risk score categories using six, seven or eight SNP combinations

| Genes | SNPs | No of risk genotypes | No of individuals | Weight change (%) | P-value | Variance explained |
|---|---|---|---|---|---|---|
| GABRA2 | rs6435326, rs279858 | 4 | 11 | 5.82 +/− 4.5 | | |
| | | 5 | 8 | 8.38 +/− 4.6 | | |
| | | 6 | 3 | 15.57 +/− 4.3 | | |
| GCG, HCRTR2, TSPO, NDUFS1, CNR1, NPY | rs13429709, rs3134701, rs4142972, rs6971, rs6435326, rs806378, rs16147 | 0 | 0 | — | $1.34 \times 10^{-6}$ | 68.5 |
| | | 1 | 5 | (−)2.19 +/− 3.2 | | |
| | | 2 | 4 | 1.79 +/− 4.0 | | |
| | | 3 | 5 | 3.02 +/− 1.9 | | |
| | | 4 | 9 | 6.00 +/− 5.5 | | |
| | | 5 | 9 | 6.28 +/− 3.5 | | |
| | | 6 | 4 | 11.45 +/− 3.1 | | |
| | | 7 | 2 | 17.85 +/− 2.2 | | |
| GCG, HCRTR2, TSPO, NDUFS1, CNR1, NPY, MC4R | rs13429709, rs3134701, rs4142972, rs6971, rs6435326, rs806378, rs16147, rs489693 | 0 | 0 | — | $5.48 \times 10^{-6}$ | 68.1 |
| | | 1 | 5 | (−)2.20 +/− 3.2 | | |
| | | 2 | 3 | 2.38 +/− 4.6 | | |
| | | 3 | 6 | 2.52 +/− 2.1 | | |
| | | 4 | 7 | 4.68 +/− 5.2 | | |
| | | 5 | 9 | 5.92 +/− 3.3 | | |
| | | 6 | 4 | 11.16 +/− 3.2 | | |
| | | 7 | 2 | 13.65 +/− 3.8 | | |
| | | 8 | 1 | 19.3 | | |
| GCG, HCRTR2, TSPO, NDUFS1, CNR1, NPY | rs13429709, rs3134701, rs4142972, rs6971, rs6435326, rs806378, rs16147 | Low risk (0, 1, 2 or 3) | 14 | .81 +/− 3.7 | $4.23 \times 10^{-7}$ | 61.4 |
| | | Intermediate risk (4 or 5) | 18 | 6.13 +/− 4.5 | | |
| | | High risk (6 or 7) | 6 | 13.59 +/− 4.2 | | |
| GCG, HCRTR2, TSPO, NDUFS1, CNR1, NPY, MC4R | rs13429709, rs3134701, rs4142972, rs6971, rs6435326, rs806378, rs16147, rs489693 | Low risk (0, 1, 2 or 3) | 14 | .81 +/− 3.7 | $3.81 \times 10^{-7}$ | 62.5 |
| | | Intermediate risk (4 or 5) | 16 | 5.38 +.− 4.1 | | |
| | | High risk (6, 7 or 8) | 7 | 13.05 +/− 4.1 | | |
| GCG, HCRTR2, NDUFS1, CNR1, NPY, MC4R | rs13429709, rs3134701, rs4142972, rs6435326, rs806378, rs16147, rs489693 | 0 | 2 | (−)4.38 +/− 4.5 | $4 \times 10^{-6}$ | 69.1 |
| | | 1 | 3 | (−)0.73 +/− 1.3 | | |
| | | 2 | 6 | 2.46 +/− 3.3 | | |
| | | 3 | 6 | 2.01 +/− 2.3 | | |
| | | 4 | 10 | 6.81 +/− 4.3 | | |
| | | 5 | 6 | 8.35 +/− 4.8 | | |
| | | 6 | 3 | 11.72 +/− 4.3 | | |
| | | 7 | 1 | 19.39# | | |
| GCG, HCRTR2, NDUFS1, CNR1, NPY, MC4R | rs13429709, rs3134701, rs4142972, rs6435326, rs806378, rs16147, rs489693 | Low risk (0 or 1) | 5 | (−)2.19 +/− 3.2 | $3.0 \times 10^{-6}$ | 57.1 |
| | | Intermediate risk (2, 3, 4) | 22 | 4.31 +/− 4.1 | | |
| | | High risk (5, 6, 7) | 10 | 10.47 +/− 5.4 | | | p-value = $1.0 \times 10^{-6}$, variance explained 69.9 when merging the seven allele group with six allele group. Note that for other entries on this table, no merging of groups was done unless specified. For example, where the risk genotypes are merged into 3 groups, low, intermediate, and high risk. Since variance is partly dependent on the number of groups, the variance for collapsed versus non-collapsed groups will differ.

TABLE 17

Analysis of the risk models associated with antipsychotic induced weight gain in subjects treated with antipsychotics with low weight gain risk.

| Genes | SNPs | No of risk genotypes | No of individuals | Weight change (%) | P-value |
|---|---|---|---|---|---|
| GCG, HCRTR2, TSPO, NDUFS1 | rs13429709, rs3134701, rs4142972, rs6971, rs6435326 | 0 | 3 | 1.42 +/− 5.2 | 0.864 |
| | | 1 | 8 | 5.0 +/− 5.5 | |
| | | 2 | 6 | 2.45 +/− 4.3 | |
| | | 3 | 11 | 3.28 +/− 5.0 | |
| | | 4 | 2 | 2.94 +/− 3.0 | |
| | | 5 | — | — | |
| GCG, HCRTR2, TSPO, NDUFS1, CNR1 | rs13429709, rs3134701, rs4142972, rs6971, rs6435326, rs806378 | 0 | 3 | 1.42 +/− 5.2 | 0.933 |
| | | 1 | 4 | 6.17 +/− 4.5 | |
| | | 2 | 4 | 3.98 +/− 6.8 | |
| | | 3 | 8 | 3.60 +/− 4.5 | |
| | | 4 | 6 | 4.65 +/− 3.6 | |
| | | 5 | 2 | 2.94 +/− 3.0 | |

TABLE 17-continued

Analysis of the risk models associated with antipsychotic induced weight gain in subjects treated with antipsychotics with low weight gain risk.

| Genes | SNPs | No of risk geno-types | No of in-divid-uals | Weight change (%) | P-value |
|---|---|---|---|---|---|
| GCG, HCRTR2, TSPO, NDUFS1, CNR1, NPY | rs13429709, rs3134701, rs4142972, rs6971, rs6435326, rs806378, rs16147 | 6 0 1 2 3 4 5 6 7 | — 4 4 5 9 4 1 — | — 1.55 +/− 4.2 9.18 +/− 4.8 3.26 +/− 4.4 3.89 +/− 4.1 2.06 +/− 2.8 5.06 | 0.349 |
| GCG, HCRTR2, TSPO, NDUFS1, CNR1, NPY, MC4R | rs13429709, rs3134701, rs4142972, rs6971, rs6435326, rs806378, rs16147, rs489693 | 0 1 2 3 4 5 6 7 8 | — 2 4 6 8 4 2 — — | — 0.15 +/− 2.5 4.22 +/− 4.4 7.00 +/− 5.8 3.05 +/− 3.8 2.91 +/− 4.5 5.7 +/− 0.9 | 0.861 |
| GCG, HCRTR2, | rs13429709, | Low risk | 13 | 4.55 +/− 5.3 | 0.928 |
| TSPO, NDUFS1, CNR1, NPY | rs3134701, rs4142972, rs6971, rs6435326, rs806378, rs16147 | (0, 1, 2 or 3) Inter-mediate risk (4 or 5) High risk (6 or 7) | 13 1 | 3.33 +/− 3.8 5.06 | |
| GCG, HCRTR2, TSPO, NDUFS1, CNR1, NPY, MC4R | rs13429709, rs3134701, rs4142972, rs6971, rs6435326, rs806378, rs16147, rs489693 | Low risk (0, 1, 2 or 3) Inter-mediate risk (4 or 5) High risk (6, 7 or 8) | 12 12 2 | 4.93 +/− 5.3 3.00 +/− 3.9 5.70 +/− 0.9 | 0.990 |

TABLE 18

Distribution of weight change (%) across risk score categories using pairwise combination between rs279858 in GABRA2 and SNPs in the AIWG model.

| Genes | SNPs | No. of risk genotypes | No. of individuals | Mean +/− Std. Deviation | P-value | Variance explained |
|---|---|---|---|---|---|---|
| GCG, GABRA2 | rs13429709, rs279858 | 0 | 7 | 0.03 +/− 6.4 | 0.0017 | 25.4 |
| | | 1 | 25 | 3.34 +/− 5.6 | | |
| | | 2 | 28 | 6.48 +/− 5.5 | | |
| HCRTR2, GABRA2 | rs3134701, rs279858 | 0 | 7 | −1.73 +/− 3.4 | 0.0041 | 23 |
| | | 1 | 21 | 2.96 +/− 4.8 | | |
| | | 2 | 32 | 6.72 +/− 5.9 | | |
| HCRTR2, GABRA2 | rs4142972, rs279858 | 0 | 9 | −0.82 +/− 3.7 | 0.0042 | 23 |
| | | 1 | 32 | 4.11 +/− 5.6 | | |
| | | 2 | 19 | 7.41 +/− 5.8 | | |
| TSPO, GABRA2 | rs6971, rs279858 | 0 | 7 | 1.3 +/− 5.5 | 0.0114 | 20.5 |
| | | 1 | 27 | 2.59 +/− 4.6 | | |
| | | 2 | 25 | 7.36 +/− 6.4 | | |
| NDUFS1, GABRA2 | rs6435326, rs279858 | 0 | 5 | 0.95 +/− 7.2 | 0.0114 | 28.4 |
| | | 1 | 19 | 3.91 +/− 4.4 | | |
| | | 2 | 14 | 8.86 +/− 5.9 | | |
| CNR1, GABRA2 | rs806378, rs279858 | 0 | 6 | −1.81 +/− 3.9 | 0.0020 | 24.3 |
| | | 1 | 28 | 3.21 +/− 4.9 | | |
| | | 2 | 25 | 7.5 +/− 5.9 | | |
| NPY, GABRA2 | rs16147, rs279858 | 0 | 4 | −3.03 +/− 4.3 | 0.0011 | 27.6 |
| | | 1 | 22 | 3.19 +/− 4.9 | | |
| | | 2 | 32 | 6.52 +/− 5.9 | | |
| MC4R, GABRA2 | rs489693, rs279858 | 0 | 10 | 0.74 +/− 5.4 | 0.0144 | 19.8 |
| | | 1 | 41 | 4.78 +/− 5.5 | | |
| | | 2 | 4 | 11.71 +/− 5.4 | | |

The present invention has been described with regard to one or more embodiments. However, it will be apparent to persons skilled in the art that a number of variations and modifications can be made without departing from the scope of the invention as defined in the claims.

What is claimed is:

1. A method of treating a subject in need of treatment with an antipsychotic medication, the method comprising
determining the subject's genotype for at least two single nucleotide polymorphisms (SNPs) defined by rs13429709 (SEQ ID NO: 1) (GCG) and rs3134701 (SEQ ID NO: 2) (HCRTR2),
identifying the subject as at high risk for antipsychotic medication induced weight gain where the subject's genotype is C/C or C/T at rs13429709 (SEQ ID NO: 1) (GCG) and A/A at rs3134701 (SEQ ID NO: 2) (HCRTR2),
identifying the subject as at intermediate risk for antipsychotic medication induced weight gain where the subject's genotype is C/C or C/T at rs13429709 (SEQ ID NO: 1) (GCG) and A/G or GG at rs3134701 (SEQ ID NO: 2) (HCRTR2), or identifying the subject as at low risk for antipsychotic medication induced weight gain where the subject's genotype is T/T at rs13429709 (SEQ ID NO: 1) (GCG) and A/G or GG at rs3134701 (SEQ ID NO: 2) (HCRTR2),
and
(i) administering to the subject identified as high risk an antipsychotic medication selected from one or more of haloperidol, perphenazine, thioridazine, ziprasidone, aripiprazole, chlorpromazine, amisulpride, fluphenazine, molindone, loxapine, iloperidone, asenapine, and lurasidone, or selected from risperidone, paliperidone, and quetiapine in combination with weight monitoring;
(ii) administering to the subject identified as intermediate risk an antipsychotic medication selected from one or more of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, and lurasidone, or selected from clozapine and olanzapine in combination with weight monitoring; or
(iii) administering to the subject identified as low risk an antipsychotic medication selected from one or more of risperidone, quetiapine, haloperidol, perphenazine, thioridazine, ziprasidone, aripiprazole, chlorpromazine, amisulpride, fluphenazine, molindone, loxapine, paliperidone, iloperidone, asenapine, lurasidone, clozapine, and olanzapine.

2. The method of claim 1, wherein the method further comprises determining the subject's genotype for at least one additional SNP selected from the group consisting of rs4142972 (SEQ ID NO: 3) (HCRTR2^2), rs6435326 (SEQ ID NO: 6) (NDUFS1), and rs6971 (SEQ ID NO: 9) (TSPO).

3. The method of claim 2, wherein the method comprises determining the subject's genotype for a set of three SNPs selected from the group consisting of
rs13429709 (SEQ ID NO: 1) (GCG), rs3134701 (SEQ ID NO: 2) (HCRTR2), rs4142972 (SEQ ID NO: 3) (HCRTR2^2);
rs13429709 (SEQ ID NO: 1) (GCG), rs3134701 (SEQ ID NO: 2) (HCRTR2), rs6435326 (SEQ ID NO: 6) (NDUFS1); and
rs13429709 (SEQ ID NO: 1) (GCG), rs3134701 (SEQ ID NO: 2) (HCRTR2), rs6971 (SEQ ID NO: 9) (TSPO).

4. The method of claim 1, wherein the method further comprises determining the subject's genotype for at least two additional SNPs selected from the group consisting of rs4142972 (SEQ ID NO: 3) (HCRTR2^2), rs6435326 (SEQ ID NO: 6) (NDUFS1), and rs6971 (SEQ ID NO: 9) (TSPO).

5. The method of claim 4, wherein the method comprises determining the subject's genotype for a set of four SNPs selected from the group consisting of
rs13429709 (SEQ ID NO: 1) (GCG), rs3134701 (SEQ ID NO: 2) (HCRTR2), rs4142972 (SEQ ID NO: 3) (HCRTR2^2), rs6435326 (SEQ ID NO: 6) (NDUFS1);
rs13429709 (SEQ ID NO: 1) (GCG), rs3134701 (SEQ ID NO: 2) (HCRTR2), rs4142972 (SEQ ID NO: 3) (HCRTR2^2), rs6971 (SEQ ID NO: 9) (TSPO); and
rs13429709 (SEQ ID NO: 1) (GCG), rs3134701 (SEQ ID NO: 2) (HCRTR2), rs6435326 (SEQ ID NO: 6) (NDUFS1), rs6971 (SEQ ID NO: 9) (TSPO).

6. The method of claim 1, wherein the method further comprises determining the subject's genotype for three additional SNPs identified by rs4142972 (SEQ ID NO: 3) (HCRTR2^2), rs6435326 (SEQ ID NO: 6) (NDUFS1), and rs6971 (SEQ ID NO: 9) (TSPO).

7. The method of claim 6, further comprising determining the subject's genotype for rs279858 (SEQ ID NO: 14) (GABRA2).

8. The method of claim 6, further comprising determining the subject's genotype for rs806378 (SEQ ID NO: 12) (CNR1).

9. The method of claim 8, further comprising determining the subject's genotype for rs16147 (SEQ ID NO: 13) (NPY).

10. The method of claim 9, further comprising determining the subject's genotype for rs489693 (SEQ ID NO: 11) (MC4R).

* * * * *

SEQUENCE LISTING

<160> NUMBER OF SEQ ID NOS: 14

<210> SEQ ID NO 1
<211> LENGTH: 51
<212> TYPE: DNA
<213> ORGANISM: Artificial Sequence
<220> FEATURE:
<223> OTHER INFORMATION: SNP rs13429709 of human GCG gene
<220> FEATURE:
<221> NAME/KEY: misc_feature
<222> LOCATION: (26)..(26)
<223> OTHER INFORMATION: Y is read as [C/T]

<400> SEQUENCE: 1
ggctgatgcc tcactgtgtg tgtccygaga tgttctcaag gttttgactt t    51

<210> SEQ ID NO 2
<211> LENGTH: 51
<212> TYPE: DNA
<213> ORGANISM: Artificial Sequence
<220> FEATURE:
<223> OTHER INFORMATION: SNP rs3134701 of human HCRTR2 gene
<220> FEATURE:
<221> NAME/KEY: misc_feature
<222> LOCATION: (26)..(26)
<223> OTHER INFORMATION: R is read as [A/G]

<400> SEQUENCE: 2
tgatgaacaa cagaaatttg tttccractg ttttggagac tgggaagtcc a    51

<210> SEQ ID NO 3
<211> LENGTH: 51
<212> TYPE: DNA
<213> ORGANISM: Artificial Sequence
<220> FEATURE:
<223> OTHER INFORMATION: SNP rs4142972 of human HCRTR2 gene
<220> FEATURE:
<221> NAME/KEY: misc_feature
<222> LOCATION: (26)..(26)
<223> OTHER INFORMATION: R is read as [A/G]

<400> SEQUENCE: 3
agcattcatg aacaaattcc tgtgcraaga ttgagaatga aagatgaata a    51

<210> SEQ ID NO 4
<211> LENGTH: 51
<212> TYPE: DNA
<213> ORGANISM: Artificial sequence
<220> FEATURE:
<223> OTHER INFORMATION: SNP rs6922310 of human HCRTR2 gene
<220> FEATURE:
<221> NAME/KEY: misc_feature
<222> LOCATION: (26)..(26)
<223> OTHER INFORMATION: R is read as [A/G]

<400> SEQUENCE: 4
acatgcccag cttcagaaat gagtcrtgat ttttctaaag caacaatatc a    51

<210> SEQ ID NO 5
<211> LENGTH: 51
<212> TYPE: DNA
<213> ORGANISM: Artificial sequence
<220> FEATURE:
<223> OTHER INFORMATION: SNP rs2653350 of human HCRTR2 gene
<220> FEATURE:
<221> NAME/KEY: misc_feature
<222> LOCATION: (26)..(26)
<223> OTHER INFORMATION: R is read as [A/G]

<400> SEQUENCE: 5
tctccttaaa acttaacttt ttgccraatt agtcaaaagc aatttctttta c      51

<210> SEQ ID NO 6
<211> LENGTH: 51
<212> TYPE: DNA
<213> ORGANISM: Artificial Sequence
<220> FEATURE:
<223> OTHER INFORMATION: SNP rs6435326 is human NDUFS1 gene
<220> FEATURE:
<221> NAME/KEY: misc_feature
<222> LOCATION: (26)..(26)
<223> OTHER INFORMATION: W is read as [A/T]

<400> SEQUENCE: 6
ggaataactc cttttgtaat aaagawagat ttaaatgaag ttaaaagtgc a      51

<210> SEQ ID NO 7
<211> LENGTH: 51
<212> TYPE: DNA
<213> ORGANISM: Artificial sequence
<220> FEATURE:
<223> OTHER INFORMATION: SNP rs1053517 of human NDUFS1 gene
<220> FEATURE:
<221> NAME/KEY: misc_feature
<222> LOCATION: (26)..(26)
<223> OTHER INFORMATION: Y is read as [C/T]

<400> SEQUENCE: 7
ataaggtttt agaataatag tatgtyacaa tatctttaaa aacagcaggt g      51

<210> SEQ ID NO 8
<211> LENGTH: 51
<212> TYPE: DNA
<213> ORGANISM: Artificial sequence
<220> FEATURE:
<223> OTHER INFORMATION: SNP rs1801318 of human NDUFS1 gene
<220> FEATURE:
<221> NAME/KEY: misc_feature
<222> LOCATION: (26)..(26)
<223> OTHER INFORMATION: R is read as [A/G]

<400> SEQUENCE: 8
ttgaggcacc actgttaat gctagrattc gaaagaggtt ggtaatagta t      51

<210> SEQ ID NO 9
<211> LENGTH: 51
<212> TYPE: DNA
<213> ORGANISM: Artificial sequence
<220> FEATURE:
<223> OTHER INFORMATION: SNP rs6971 of human TSPO gene
<220> FEATURE:
<221> NAME/KEY: misc_feature
<222> LOCATION: (26)..(26)
<223> OTHER INFORMATION: Y is read as [C/T]

<400> SEQUENCE: 9
catacgcagt agttgagtgt ggtcgygaag gccagccagg ccaggtaggg g      51

<210> SEQ ID NO 10
<211> LENGTH: 51
<212> TYPE: DNA
<213> ORGANISM: Artificial sequence
<220> FEATURE:
<223> OTHER INFORMATION: SNP rs2268639 of human GLPR1 gene
<220> FEATURE:
<221> NAME/KEY: misc_feature
<222> LOCATION: (26)..(26)
<223> OTHER INFORMATION: W is read as [A/T]

```
<400> SEQUENCE: 10
tgagaaacgg ggacgtgggg gggtcwagat gacaaggtgg cagcagggag c          51

<210> SEQ ID NO 11
<211> LENGTH: 51
<212> TYPE: DNA
<213> ORGANISM: Artificial sequence
<220> FEATURE:
<223> OTHER INFORMATION: SNP rs489693 is human MC4R gene
<220> FEATURE:
<221> NAME/KEY: misc_feature
<222> LOCATION: (26)..(26)
<223> OTHER INFORMATION: M is read as [A/C]

<400> SEQUENCE: 11
tcttaattct gttgtcatta gttccmgttt gttaaatgtt tacagcgtgg c          51

<210> SEQ ID NO 12
<211> LENGTH: 51
<212> TYPE: DNA
<213> ORGANISM: Artificial sequence
<220> FEATURE:
<223> OTHER INFORMATION: SNP rs806378 of human CNR1 gene
<220> FEATURE:
<221> NAME/KEY: misc_feature
<222> LOCATION: (26)..(26)
<223> OTHER INFORMATION: Y is read as [C/T]

<400> SEQUENCE: 12
ccctctatta caggcctcat cacgtygtat aatcaggagt tcacatattt a          51

<210> SEQ ID NO 13
<211> LENGTH: 51
<212> TYPE: DNA
<213> ORGANISM: Artificial sequence
<220> FEATURE:
<223> OTHER INFORMATION: SNP rs16147 of human NPY gene
<220> FEATURE:
<221> NAME/KEY: misc_feature
<222> LOCATION: (26)..(26)
<223> OTHER INFORMATION: R is read as [A/G]

<400> SEQUENCE: 13
ttgtctcctg ccaacaggac taccarccca ctgggtgccg gagtaggaag c          51

<210> SEQ ID NO 14
<211> LENGTH: 52
<212> TYPE: DNA
<213> ORGANISM: Artificial Sequence
<220> FEATURE:
<223> OTHER INFORMATION: SNP rs279858 of human GABRA2 gene
<220> FEATURE:
<221> NAME/KEY: misc_feature
<222> LOCATION: (27)..(27)
<223> OTHER INFORMATION: Y is read as [T/C]

<400> SEQUENCE: 14
attgtcatat tatgagctac tgatttyttc ccattgtgaa aaaggtatc tg          52
```